United States Patent
Wong

(10) Patent No.: US 12,306,159 B2
(45) Date of Patent: May 20, 2025

(54) METHODS FOR MEASURING FUGITIVE EMISSION RATES

(71) Applicant: Colin Irvin Wong, Burnaby (CA)

(72) Inventor: Colin Irvin Wong, Burnaby (CA)

(*) Notice: Subject to any disclaimer, the term of this patent is extended or adjusted under 35 U.S.C. 154(b) by 0 days.

(21) Appl. No.: 18/896,520

(22) Filed: Sep. 25, 2024

(65) Prior Publication Data

US 2025/0110093 A1    Apr. 3, 2025

Related U.S. Application Data

(60) Provisional application No. 63/677,569, filed on Jul. 31, 2024, provisional application No. 63/587,435, filed on Oct. 2, 2023.

(51) Int. Cl.
| | |
|---|---|
| *G01N 33/00* | (2006.01) |
| *B64U 20/80* | (2023.01) |
| *G01F 1/58* | (2006.01) |
| *G01N 21/17* | (2006.01) |
| *G01N 21/85* | (2006.01) |
| *B64U 101/35* | (2023.01) |

(52) U.S. Cl.
CPC ......... *G01N 33/0019* (2024.05); *B64U 20/80* (2023.01); *G01F 1/58* (2013.01); *G01N 21/17* (2013.01); *G01N 21/85* (2013.01); *B64U 2101/35* (2023.01); *G01N 2021/1795* (2013.01); *G01N 2021/8578* (2013.01)

(58) Field of Classification Search
CPC .... G01N 33/0019; G01N 21/17; G01N 21/85; G01N 2021/1795; G01N 2021/8578; B64U 20/80; B64U 2101/35; G01F 1/58
USPC .......................................................... 73/31.01
See application file for complete search history.

(56) References Cited

U.S. PATENT DOCUMENTS

| | | | |
|---|---|---|---|
| 4,135,092 A | 1/1979 | Milly | |
| 4,204,121 A | 5/1980 | Milly | |
| 6,542,242 B1 | 4/2003 | Yost et al. | |
| 8,294,899 B2 | 10/2012 | Wong | |
| 8,781,755 B2 * | 7/2014 | Wong | G01W 1/10 |
| | | | 702/22 |
| 10,416,672 B2 | 9/2019 | Knudsen | |
| 10,677,771 B2 | 6/2020 | Dittberner et al. | |

(Continued)

FOREIGN PATENT DOCUMENTS

| | | |
|---|---|---|
| CA | 2715677 C | 11/2011 |
| CA | 2655279 C | 2/2018 |

OTHER PUBLICATIONS

Abichou et al., "Using Ground and Drone-Based Surface Emission Monitoring (SEM) Data to Locate and Infer Landfill Methane Emissions", 2023.

(Continued)

*Primary Examiner* — Nathaniel T Woodward
(74) *Attorney, Agent, or Firm* — Roni M. Jones; Oyen Wiggs Green & Mutala LLP

(57) ABSTRACT

A method of determining a flow rate of airborne matter of a plume from an emission source through a notional surface. The method comprises obtaining a plurality of mass ratio measurements along a sampling surface and determining a mass flow rate of the airborne matter of the plume through at least a portion of the notional surface based at least in part on the plurality of mass ratio measurements, wherein the sampling surface and the notional surface are non-parallel.

20 Claims, 14 Drawing Sheets

(56) References Cited

U.S. PATENT DOCUMENTS

| | | | |
|---|---|---|---|
| 11,614,430 B2 | 3/2023 | Buckingham et al. | |
| 11,940,817 B2 | 3/2024 | Kreitinger et al. | |
| 12,066,353 B2 | 8/2024 | Thorpe et al. | |
| 2014/0236521 A1* | 8/2014 | Wong | G01P 21/02 702/100 |
| 2021/0140934 A1 | 5/2021 | Smith et al. | |
| 2023/0160789 A1* | 5/2023 | Donnat | B64U 20/80 73/31.05 |
| 2023/0207070 A1* | 6/2023 | Donnat | G01N 33/0004 702/22 |

OTHER PUBLICATIONS

Bel Hadj Ali, et al., "Comparing estimates of fugitive landfill methane emissions using inverse plume modeling obtained with Surface Emission Monitoring (SEM), Drone Emission Monitoring (DEM), and Downwind Plume Emission Monitoring (DWPEM)", 2020.

Wong et al., "Methane Collection and Oxidation Efficiency Assessment at the Cache Creek Landfill", 2010.

Desjardins et al., "Evaluation of a micrometeorological mass balance method employing an open-path laser for measuring methane emissions", 2004.

Fosco et al., "Progress in monitoring methane emissions from landfills using drones: an overview of the last ten years", 2024.

Shaw et al., "Methods for quantifying methane emissions using unmanned aerial vehicles: a review", 2021.

Yong et al., "Lessons learned from a UAV survey and methane emissions calculation at a UK landfill", 2024.

Abichou et al., "Estimation of total landfill surface methane emissions using geospatial approach combined with measured surface ambient air methane concentrations", 2023.

Galfalk et.al., "Sensitive Drone Mapping of Methane Emissions without the Need for Supplementary Ground-Based Measurements", 2021.

Mukhartova et.al., "Inverse problem for retrieving greenhouse gas fluxes at the non-uniform underlying surface from measurements of their concentrations at several levels", 2024.

Bolek et al., "UAV-based in situ measurements of CO2 and CH4 fluxes over complex natural ecosystems", 2024.

* cited by examiner

METHODS FOR MEASURING FUGITIVE EMISSION RATES

CROSS-REFERENCE TO RELATED APPLICATIONS

This application claims priority from, and for the purposes of the United States the benefit under 35 USC 119 in relation to, U.S. provisional patent application No. 63/587,435 filed 2 Oct. 2023 and U.S. provisional patent application No. 63/677,569 filed 31 Jul. 2024, all of which are hereby incorporated herein by reference.

TECHNICAL FIELD

This invention relates to methods for measuring fugitive emission rates of airborne matter of an emission plume, and in particular to methods for employing aerial vehicles (such as unmanned aerial vehicles) for measuring fugitive emission rates of airborne matter of an emission plume where the aerial vehicles are subject to a maximum or minimum operating altitude.

BACKGROUND OF THE INVENTION

Fugitive emissions result from releases of airborne matter to the atmosphere from one or more emission sources such as, for example, smokestacks, flares, wells, leaks, vents, landfills, reservoirs, effluent ponds, mines, natural deposits, cities, industrial plants, herds of animals, etc. The airborne matter may be, for example, greenhouse gases, polluting gases, or particulate matter. The measurement of the mass flow rate of airborne matter from emission sources is of interest to, for example, government authorities that regulate air emissions and private entities tracking their emissions.

Aerial vehicles, including manned aerial vehicles and unmanned aerial vehicles ("UAVs") such as drones, may present a potentially useful, safe and cost-effective platform for sampling the atmosphere for airborne matter to facilitate measurement of the mass flow rate (or the equivalent volumetric flow rate) of airborne matter from emission sources. However, the maximum operating altitude of aerial vehicles may be limited. For example, regulations such as those in Canada and the United States may restrict the maximum altitude at which aerial vehicles may be operated without costly and/or inconvenient permissions. Likewise, for some aerial vehicles the maximum operating altitude is limited by the inherent capabilities of the vehicle. Thus, aerial vehicles may have limited effectiveness when a plume of airborne matter extends beyond the maximum operating altitude (whether due to regulations, safety or the inherent capabilities of the vehicle).

There is accordingly a desire for effective, accurate and practical methods to employ aerial vehicles to measure fugitive emission rates of a plume where the plume extends above the maximum operating altitude.

Similarly, aerial vehicles may be limited as to how low they can operate. Again, this minimum operating altitude may be due to government regulations, safety or the inherent limitations of the vehicle.

There is accordingly a desire for effective, accurate and practical methods to employ aerial vehicles to measure fugitive emission rates of a plume where the plume extends below the minimum operating altitude of the vehicle.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a method of determining a flow rate of airborne matter of a plume from an emission source through a notional surface. The method comprises obtaining a plurality of mass ratio measurements along a sampling surface and
determining a mass flow rate of the airborne matter of the plume through at least a portion of the notional surface based at least in part on the plurality of mass ratio measurements, wherein the sampling surface and the notional surface are non-parallel.

Another aspect of the invention provides a method of determining a flow rate of airborne matter of a plume from an emission source through a notional surface. The method comprises obtaining a plurality of mass ratio measurements along a sampling surface upwind of the notional surface, determining a mass flow rate of the airborne matter of the plume through a portion of the notional surface that is above an altitude of the sampling surface based at least in part on the plurality of mass ratio measurements, wherein the sampling surface and the notional surface are non-parallel.

Another aspect of the invention comprises a method of determining a flow rate of airborne matter of a plume from an emission source through a notional surface. The method comprises obtaining a plurality of mass ratio measurements along a sampling surface downwind of the notional surface and determining a mass flow rate of the airborne matter of the plume through a portion of the notional surface that is below an altitude of the sampling surface based at least in part on the plurality of mass ratio measurements wherein the sampling surface and the notional surface are non-parallel.

Another aspect of the invention provides a method of determining a flow rate of airborne matter of a plume from an emission source through a notional surface. The method comprises obtaining a plurality of mass ratio measurements along a sampling surface and determining a mass flow rate of the airborne matter of the plume through the notional surface based at least in part on the plurality of mass ratio measurements, wherein a wind flow direction through the notional surface is non-parallel to the notional surface.

Another aspect of the invention provides a method of determining a flow rate of airborne matter of a plume from an emission source through a notional surface. The method comprises obtaining a plurality of mass ratio measurements along a sampling surface and determining a mass flow rate of the airborne matter of the plume through the notional surface based at least in part on the plurality of mass ratio measurements, wherein a wind flow direction through the notional surface is substantially parallel to the sampling surface.

In some embodiments, the notional surface is generally orthogonal to a wind flow direction. In some embodiments, the notional surface is orthogonal to a wind flow direction through the notional surface. In some embodiments, the notional surface is substantially vertical. In some embodiments, the notional surface extends generally vertically. In some embodiments, the notional surface is at an angle of between approximately 0° and 60° to the vertical.

In some embodiments, the sampling surface is generally parallel to the wind flow direction. In some embodiments, the sampling surface and the notional surface are substantially orthogonal. In some embodiments, the sampling surface is substantially horizontal. In some embodiments, the sampling surface extends generally horizontally. In some embodiments, the sampling surface is at an angle of between approximately 0° and 60° to the horizontal. In some embodiments, an altitude of the sampling surface is limited by an operation ceiling, the altitude of the operation ceiling being below an intersection of an upwind edge of the plume with the notional surface. In some embodiments, the sampling surface is upwind of the notional surface. In some embodiments, an altitude of the sampling surface is limited by an operation floor, the altitude of the operation floor being above an intersection of a downwind edge of the plume with the notional surface. In some embodiments, an altitude of the sampling surface is between approximately 90 m and 400 m. In some embodiments, the sampling surface is downwind of the notional surface. In some embodiments, the sampling surface is substantially planar. In some embodiments, the sampling surface is non-planar. In some embodiments, the sampling surface corresponds in shape to a ground surface below the sampling surface. In some embodiments, a shape of the sampling surface mimics the wind flow at the sampling surface. In some embodiments, an upwind boundary of the sampling surface is at least as far upwind as an upwind edge of the emission source. In some embodiments, an upwind boundary of the sampling surface is at least as far upwind as an upwind edge of the plume. In some embodiments, a downwind boundary of the sampling surface is at least as far downwind as a downwind edge of the emission source. In some embodiments, a downwind boundary of the sampling surface is at least as far downwind as the notional surface. In some embodiments, lateral boundaries of the sampling surface encompass lateral edges of the emission source. In some embodiments, lateral boundaries of the sampling surface encompass lateral edges of the plume. In some embodiments, the plume extends farther downwind than a downwind boundary of the sampling surface.

In some embodiments, obtaining a plurality of mass ratio measurements along the sampling surface comprises causing a platform to travel on a platform path along the sampling surface. In some embodiments, the platform path comprises a plurality of substantially parallel segments. In some embodiments, the substantially parallel segments are generally orthogonal to a wind flow direction. In some embodiments, the generally parallel segments are generally oriented between approximately 20° and 90° to a wind flow direction. In some embodiments, adjacent ones of the substantially parallel segments are spaced apart from one another in the wind flow direction. In some embodiments, the platform path segments are non-parallel.

In some embodiments, the platform comprises a ground based vehicle. In some embodiments, the platform comprises an aerial vehicle. In some embodiments, the platform comprises an unmanned aerial vehicle. In some embodiments, the platform comprises an instrument measuring airborne matter ("IMAM") configured to measure mass ratios. In some embodiments, the IMAM comprises an optical sensing instrument.

In some embodiments, the mass ratio comprises a point concentration. In some embodiments, the platform comprises a primary platform and a secondary platform and the primary platform comprises a transmitter of the IMAM and the secondary platform comprises a receiver of the IMAM. In some embodiments, the platform comprises a primary platform and a secondary platform and the primary platform comprises a transmitter and a receiver of the IMAM and the secondary platform comprises a reflector for reflecting a beam transmitted from the transmitter back to the receiver. In some embodiments, the platform path comprises a primary path for the primary platform and a secondary path for the secondary platform wherein the primary path and secondary path are similar in shape but spaced apart by a space. In some embodiments, the space is a horizontal space. In some embodiments, the space is a vertical space. In some embodiments, the mass ratio comprises an integrated concentration.

In some embodiments, determining the mass flow rate of the airborne matter of the plume through the at least a portion of the notional surface based at least in part on the plurality of mass ratio measurements comprises determining a first mass flow rate through a first portion of the notional surface based at least in part on the plurality of mass ratio measurements. In some embodiments, the first portion of the notional surface is a portion above the altitude of the sampling surface. In some embodiments, the first portion of the notional surface is a portion below the altitude of the sampling surface.

In some embodiments, the method comprises integrating the mass ratio measurements across the sampling surface to obtain a mass per unit length value of the airborne matter and determining the mass flow rate of the airborne matter of the plume through the at least a portion of the notional surface based at least in part on the mass per unit length value.

In some embodiments, the mass flow rate of the airborne matter of the plume through the at least a portion of the notional surface comprises the product of the mass per unit length value and a wind factor.

In some embodiments, the wind factor comprises the product of a wind speed and a scaling factor.

In some embodiments, the scaling factor is determined according to:

$$S = \frac{\lambda}{\delta}$$

where $\lambda$ is a distance between an altitude of a location where an upwind edge of the plume intersects the notional surface and the altitude of the sampling surface and $\delta$ is a distance between the notional surface and a location where the upwind edge of the plume crosses the sampling surface. In some embodiments, the altitude of the location where the upwind edge of the plume intersects the notional surface is determined by extrapolation based at least in part on a location of an intersection of the upwind edge of the plume and the sampling surface. In some embodiments, the altitude of the location where the upwind edge of the plume intersects the notional surface is determined by extrapolation based at least in part on a location of the upwind edge of the emission source. In some embodiments, the altitude of the location where the upwind edge of the plume intersects the notional surface is determined by extrapolation based at least in part on a location of the upwind edge of the plume at an altitude below the sampling surface.

In some embodiments, the scaling factor is determined according to:

$$S = \frac{\lambda}{\delta}$$

where $\lambda$ is a distance between the sampling surface and an intersection of a downwind edge of the plume with the notional surface and $\delta$ is a distance between the notional surface and a location where the downwind edge of the plume crosses the sampling surface.

In some embodiments, the scaling factor is determined according to:

$$S = \frac{\lambda}{\delta}$$

where $\lambda$ is a distance between an intersection of a downwind edge of the plume with the sampling surface and a top of the plume above the intersection of the downwind edge 20B with the sampling surface and $\delta$ is a distance between an intersection of an upwind edge of the plume with the sampling surface and the intersection of the downwind edge of the plume with the sampling surface.

In some embodiments, the location of the intersection of the downwind edge of the plume with the notional surface is determined by extrapolation based at least in part on a location of an intersection of the downwind edge of the plume and the sampling surface.

In some embodiments, the location of the intersection of the downwind edge of the plume with the notional surface is determined by extrapolation based at least in part on a location of the downwind edge of the emission source. In some embodiments, the location of the intersection of the downwind edge of the plume with the notional surface is determined by extrapolation based at least in part on a location of the downwind edge of the plume at an altitude below the sampling surface.

In some embodiments, the scaling factor is determined according to:

$$S = \frac{\lambda}{\delta}$$

where $\lambda$ is a distance between the intersection of an upwind edge of the plume with the notional surface and an intersection of a downwind edge of the plume with the notional surface and $\delta$ is a distance between an intersection of the downwind edge of the plume with the sampling surface and an intersection of the upwind edge of the plume with the sampling surface.

In some embodiments, the location of the intersection of the downwind edge of the plume with the notional surface is determined by extrapolation based at least in part on a location of the downwind edge of the plume at an altitude at or below the sampling surface. In some embodiments, the location of the intersection of the upwind edge of the plume with the notional surface is determined by extrapolation based at least in part on a location of an intersection of the upwind edge of the plume and the sampling surface. In some embodiments, the wind speed is representative of a wind speed at the notional surface between an altitude of the sampling surface and an altitude of an intersection of an upwind edge of the plume with the notional surface.

In some embodiments, the wind speed is representative of a wind speed at the notional surface between an altitude of the sampling surface and an altitude of an intersection of a downwind edge of the plume with the notional surface. In some embodiments, the wind speed is determined by direct measurement. In some embodiments, the wind speed is determined by extrapolation or modeling.

In some embodiments, determining the mass flow rate of the airborne matter of the plume through the notional surface based at least in part on the plurality of mass ratio measurements comprises determining a second mass flow rate through a second portion of the notional surface and summing the first mass flow rate and the second mass flow rate to obtain the mass flow rate of the airborne matter of the plume through the notional surface wherein the second mass flow rate is determined based at least in part on a mass balance method. In some embodiments, the second mass flow rate is determined based at least in part on a mass balance method.

In some embodiments, the method comprises obtaining a second plurality of mass ratio measurements along a second sampling surface, the second sampling surface generally parallel with the notional surface and determining the second mass flow rate based at least in part on the second plurality of mass ratio measurements.

In some embodiments, the method comprises determining a background flow rate of the airborne matter through the notional surface and determining the flow rate of airborne matter in the plume from the emission source comprises subtracting the background flow rate of the airborne matter through the notional surface a total flow rate of the airborne matter through the notional surface. In some embodiments, determining the background flow rate of the airborne matter through the notional surface comprises obtaining a third plurality of mass ratio measurements along a second sampling surface upwind of the emission source, the third sampling surface generally parallel with the notional surface and determining the background flow rate of the airborne matter through the notional surface based at least in part on the third plurality of mass ratio measurements.

In some embodiments, the method comprises obtaining background mass ratio measurements and subtracting the background mass ratio measurements from the mass ratio measurements to obtain net mass ratio measurements of airborne matter in the plume from the emission source.

In some embodiments, determining the mass flow rate of the airborne matter of the plume through the notional surface based at least in part on the plurality of mass ratio measurements comprises determining the mass flow rate of the airborne matter of the plume through the notional surface based at least in part on the plurality of net mass ratio measurements of airborne matter in the plume from the emission source.

In some embodiments, the method comprises determining a mass flow rate of the airborne matter of the plume through a portion of a second notional surface based at least in part on the mass flow rate of the airborne matter of the plume through the at least a portion of the notional surface wherein the second notional surface extends substantially parallel to the sampling surface. In some embodiments, the second notional surface is substantially coincident with the sampling surface.

Another aspect of the invention provides a method of obtaining an airborne matter flow rate, originating from an emission source of interest, for a portion of a plume above a sampling surface that is located above ground level. The method comprises measuring the airborne matter at two or more identified locations in a generally horizontal sampling surface using an IMAM, obtaining two or more concentration or integrated concentration measurements, a geographic position and altitude value for each of the two or more identified locations, mapping the concentration or integrated concentration measurements relative to the geographic position and altitude values for each of the two or more identified locations in the sampling surface to obtain an airborne matter concentration or integrated concentration distribution map in the sampling surface, and integrating the airborne matter concentrations or integrated concentrations distribution map across the sampling surface to obtain a mass per unit length value of the airborne matter in the sampling surface and obtaining an airborne matter flow rate in mass per unit time for the portion of the plume above the sampling surface based at least in part on the mass per unit length value of the airborne matter in the sampling surface. In some embodiments, the airborne matter flow rate in mass per unit time is the product of the mass per unit length value multiplied by a wind factor.

Another aspect of the invention provides a system comprising at least one server and/or processor having at least one application program and computer instructions operating thereon which are configured to cause at least one server and/or processor to perform the methods, steps and/or functions described herein.

Another aspect of the invention provides a non-transitory, computer readable medium having at least one application program or computer instructions operating thereon which are configured to cause at least one server and/or processor to perform the methods, steps and/or functions described herein.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION OF THE INVENTION

Throughout the following description specific details are set forth to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

One aspect of the invention provides a method for measuring the fugitive emission rate through a notional surface of airborne matter of a plume emitted from an emission source. The method may employ a vehicle (e.g., an aerial vehicle) to take one or more mass ratio measurements along a sampling surface. The method may be applicable despite restrictions (legal or otherwise) on the altitude above which the vehicle may operate or below which the vehicle may operate.

The method may comprise obtaining a plurality of mass ratio measurements along a sampling surface and determining a mass flow rate of the airborne matter of the plume through the notional surface based at least in part on the plurality of mass ratio measurements, wherein the sampling surface and the notional surface are non-parallel.

The method may comprise obtaining a plurality of mass ratio measurements along a sampling surface upwind of the notional surface and determining a mass flow rate of the airborne matter of the plume through a portion of the notional surface that is above an altitude of the sampling surface based at least in part on the plurality of mass ratio measurements, wherein the sampling surface and the notional surface are non-parallel.

The method may comprise obtaining a plurality of mass ratio measurements along a sampling surface downwind of the notional surface and determining a mass flow rate of the airborne matter of the plume through a portion of the notional surface that is below an altitude of the sampling surface based at least in part on the plurality of mass ratio measurements, wherein the sampling surface and the notional surface are non-parallel.

The method may comprise obtaining a plurality of mass ratio measurements along a sampling surface, determining a mass flow rate of the airborne matter of the plume through the sampling surface based at least in part on the plurality of mass ratio measurements and optionally determining the flow rate of airborne matter of the plume from the emission source through the notional surface based at least in part on the mass flow rate of the airborne matter of the plume through the sampling surface.

The method may comprise obtaining a plurality of mass ratio measurements along a sampling surface and determining a mass flow rate of the airborne matter of the plume through the notional surface based at least in part on the plurality of mass ratio measurements, wherein a wind flow direction through the notional surface is non-parallel to the notional surface.

Figure 1:
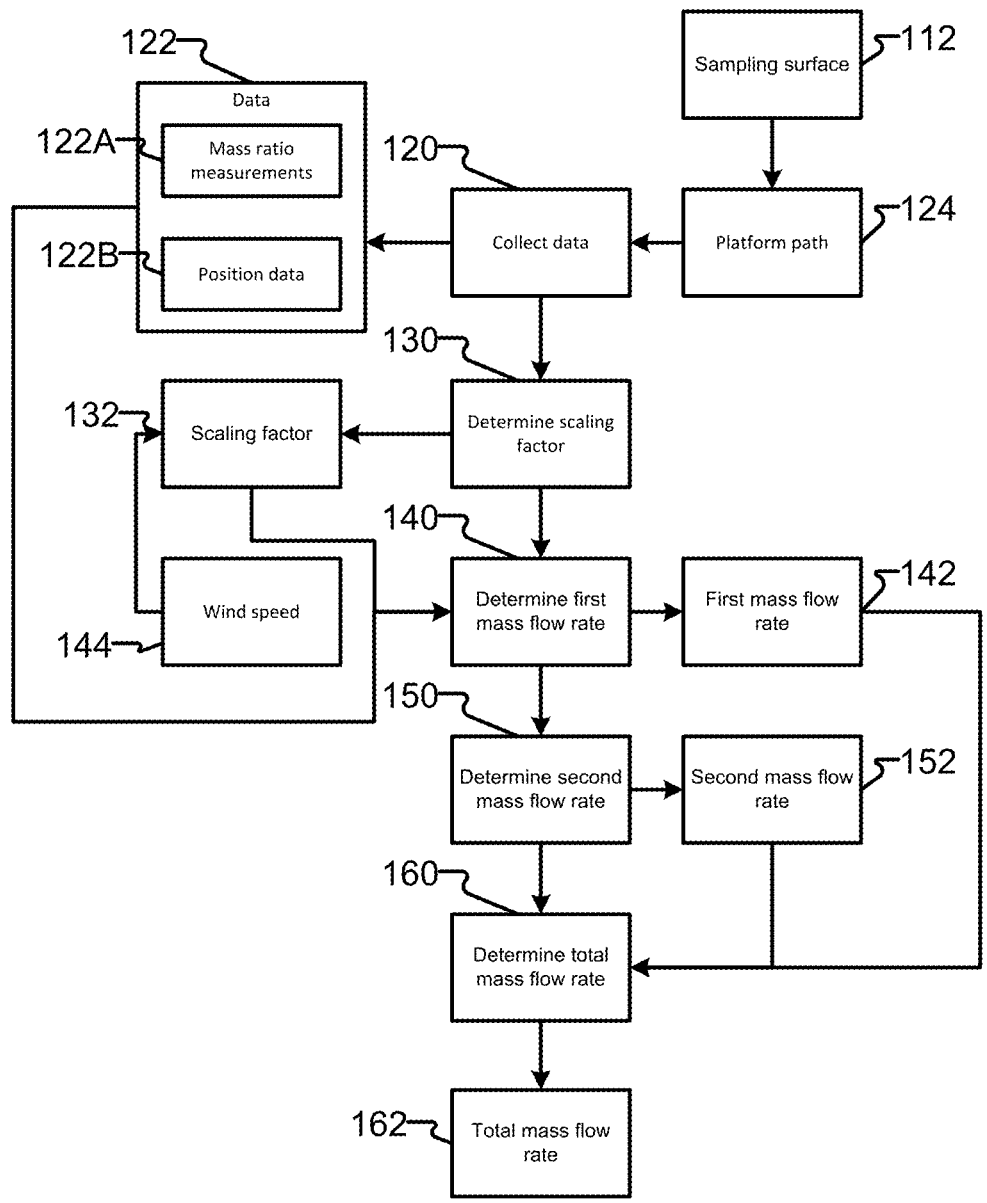
FIG. 1 depicts an exemplary method of determining a mass flow rate of airborne matter of a plume through a notional surface according to an embodiment of the invention.
Figure 2A:
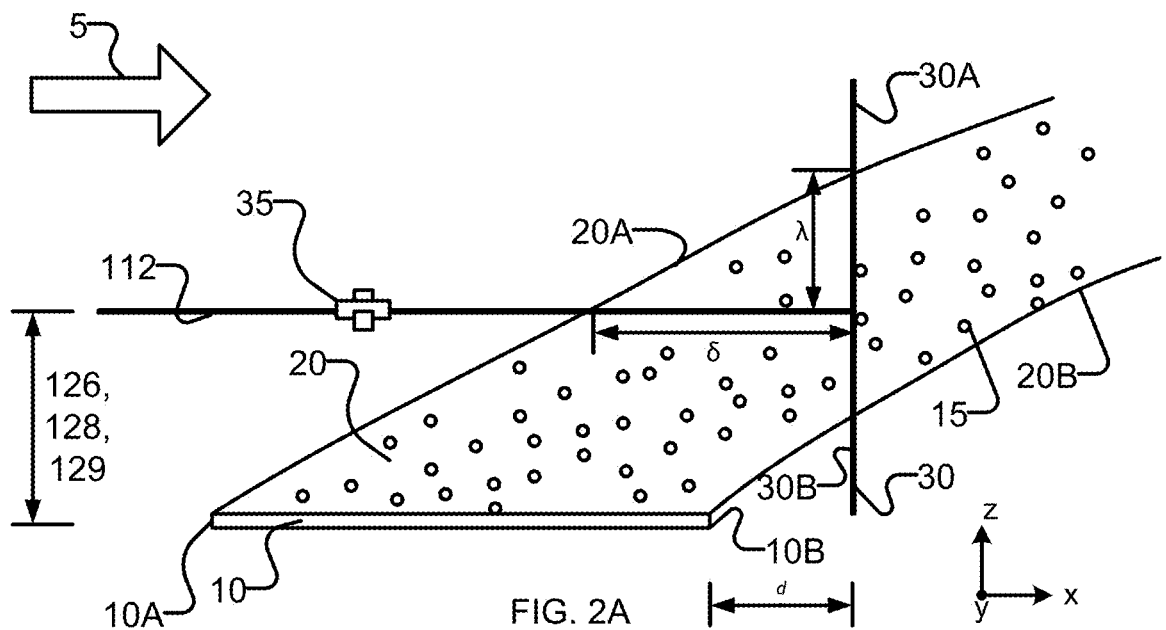
FIG. 2A is a schematic depiction of an exemplary sampling surface and an exemplary notional surface relative to an emission source according to an embodiment of the invention.
Figure 3:
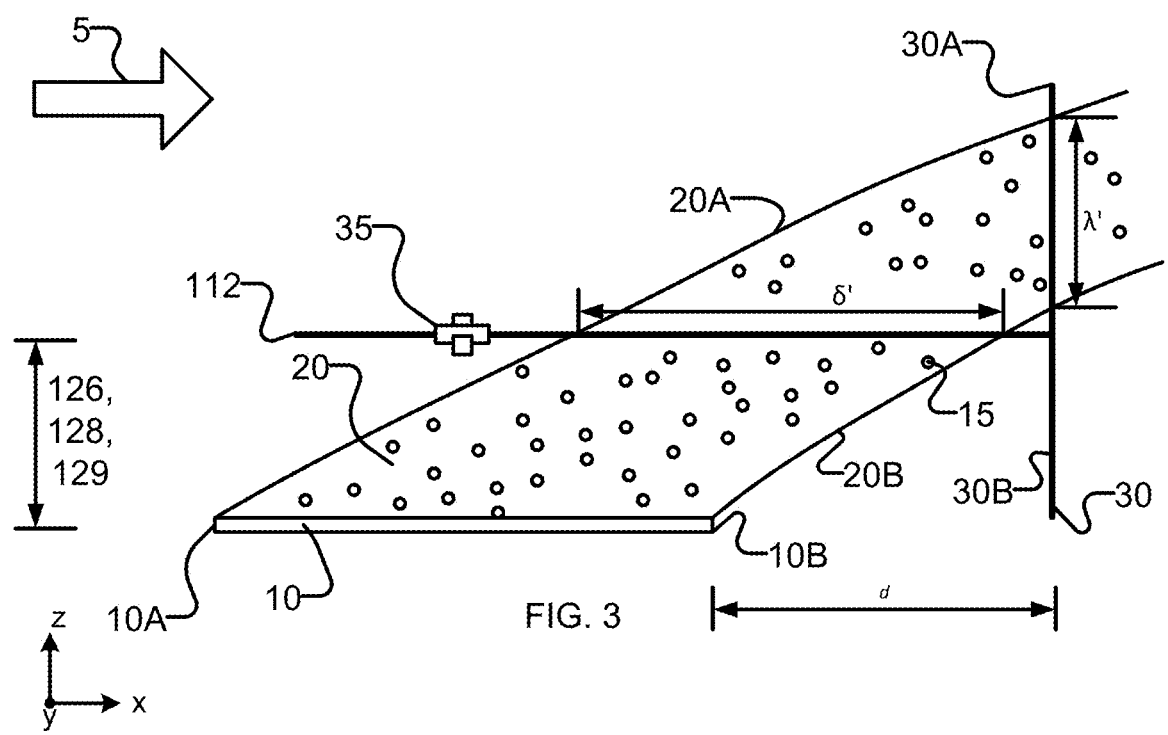
FIG. 3 is a schematic depiction of another exemplary sampling surface and another exemplary notional surface relative to an exemplary emission source according to an embodiment of the invention.

The method may comprise obtaining a plurality of mass ratio measurements along a sampling surface and determining a mass flow rate of the airborne matter of the plume through the notional surface based at least in part on the plurality of mass ratio measurements, wherein a wind flow direction through the notional surface is generally or substantially parallel to the sampling surface FIG. 1 depicts a method 100, according to an example embodiment of the invention, for measuring the fugitive emission rate of airborne matter 15 of a plume 20 through a notional surface 30 where plume 20 is emitted from an emission source 10 as shown, for example, in FIGS. 2A and 3.

Method 100 may be employed when there is an altitude restriction for flying platform 35 above a particular altitude (referred to herein as an "operation ceiling"). Such restrictions may be practical (e.g., due to inherent limitations of platform 35, weather, etc.), self-imposed (e.g., for safety or cost reasons) and/or legal (e.g., due to regulations governing operation of platform 35). For example, in or around early 2023, Canadian regulations provided an operation ceiling for drones of 122 m above ground level or 30 m above any building or structure if the drone was being operated at a distance of less than 61 m from the horizontal structure.

Figure 2B:
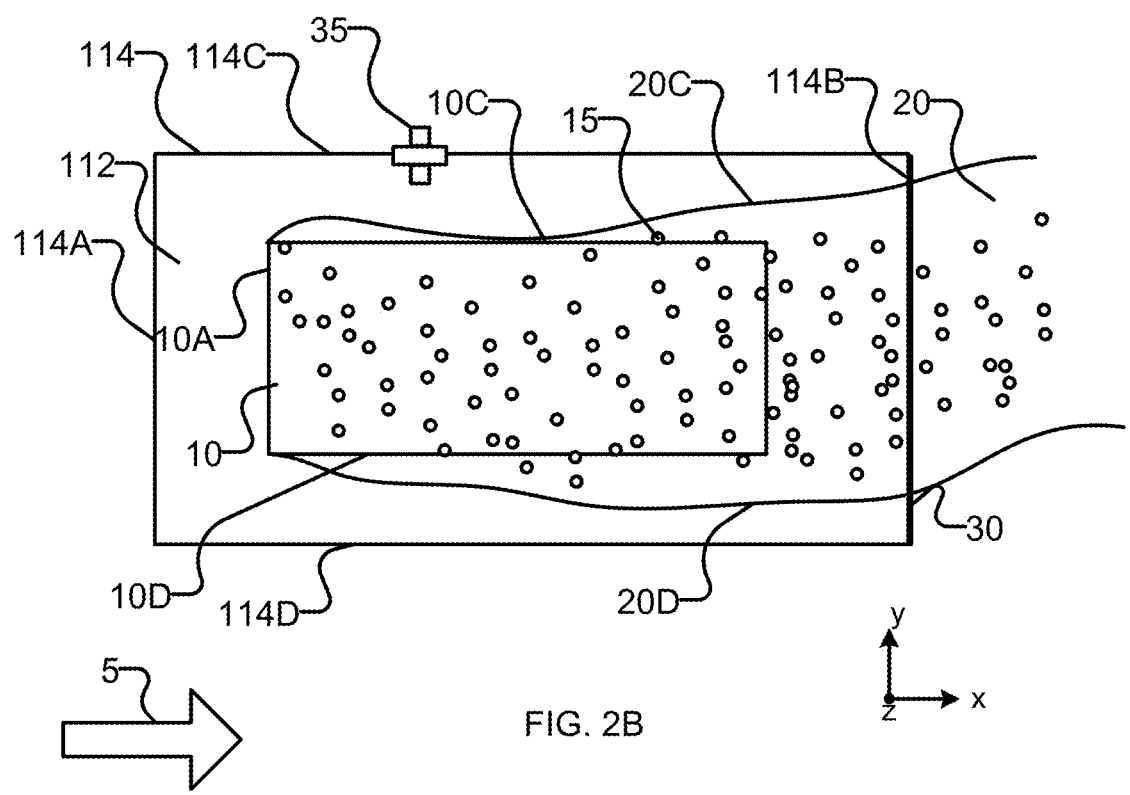
FIG. 2B is another schematic depiction of the sampling surface and the notional surface relative to the emission source of FIG. 2A.

FIGS. 2A and 2B depict an exemplary plume 20 of airborne matter 15 emitted from an emission source 10 subject to wind blowing in wind flow direction 5 wherein wind flow direction 5 points generally or substantially in the direction of travel of airborne matter 15 carried by the wind at emission source 10. For simplicity, wind flow direction 5 is depicted and described herein as being parallel to a horizontal X-direction and orthogonal to a horizontal Y-direction and a vertical Z-direction but this is not mandatory.

Emission source 10 may comprise any kind of emission source which releases airborne matter 15 in a plume 20. Emission source 10 may comprise, for example, a point source such as a smokestack, flare, well, leak (e.g., a pipeline leak), vent, etc. Emission source 10 may comprise, for example, a diffuse source such as a landfill, reservoir, effluent pond, mine, natural deposit, etc. Emission source 10 may comprise, for example, a collection of point sources such as a city, an industrial plant, a herd of animals, etc.

For convenience, the boundaries of emission source 10 are defined herein relative to the wind flow direction 5 at emission source 10. For example, as shown in FIGS. 2A and 2B, emission source 10 may comprise, in plan view (e.g., looking downward in the Z-direction), an upwind edge 10A, a downwind edge 10B and opposing lateral edges 10C and 10D. Of course, while emission source 10 is depicted as being rectangular in shape, this is done for convenience and it should be understood that emission source 10 may have any regular or irregular shape.

Plume 20 may comprise the atmospheric volume within which airborne matter 15 emitted from emission source 10 exists. Over time, plume 20 may change in shape and/or size (e.g., expand) due to advection and diffusion as it is blown by the wind.

For convenience, the boundaries of plume 20 are also defined herein relative to wind flow direction 5. For example, as shown in FIG. 2B, plume 20 may comprise, in plan view, an upwind edge 20A, a downwind edge 20B and opposing lateral edges 20C and 20D. While plume 20 is depicted with a particular shape, this is for convenience and it should be understood that plume 20 may have any shape or size. For example, plume 20 may range from a few meters in height to several hundred meters or more. Likewise, plume 20 may range from a few square meters in area to several hundred hectares or more.

Airborne matter 15 may comprise any type of airborne matter. Airborne matter 15 may comprise, for example, greenhouse gases, polluting gases, or particulate matter. Airborne matter 15 may comprise, for example, compounds, molecules, one or more gases, one or more mixtures of gases, greenhouse gasses (e.g., carbon dioxide, methane, nitrous oxide, and the like), gaseous organic compounds (e.g., combustible gasses, natural gas, methane, ethane, propane), polluting gasses (e.g., sulphur dioxide, ammonia, ozone, etc.), emissions (e.g., emissions from vehicles, landfills, industrial facilities, tailings ponds, reservoirs, oil and gas extraction facilities, mines, petrochemical plants, refineries, chemical plants or the like), radioactive emissions, toxic emissions, particulate material, aerosols, etc.

The location, size and orientation of notional surface 30 (also referred to herein simply as notional surface 30) may be based at least in part on one or more of the location, size and orientation of emission source 10, the location, size and orientation of plume 20, the geography surrounding emission source 10, wind flow direction 5, the wind speed, etc.

Notional surface 30 may comprise a generally or substantially vertical or upright surface. In other words, despite some variation, notional surface 30 may extend generally or substantially vertically (e.g., in the Z-direction). In some embodiments, notional surface 30 is oriented at an angle of between approximately 0° to 60° with respect to the vertical. In some embodiments, notional surface 30 is oriented at an angle of between approximately 0° to 45° with respect to the vertical. In some embodiments, notional surface 30 is oriented at an angle of greater than 45° with respect to the vertical. In some embodiments, notional surface 30 is oriented approximately orthogonally to wind flow direction 5 (e.g., notional surface 30 extends generally or substantially in the Y and Z-directions where wind flow direction 5 is parallel to the X-direction as depicted). Notional surface 30 may be flat but this is not mandatory.

Notional surface 30 may be located and/or sized to encompass an entire cross-sectional area of plume 20 where plume 20 intersects notional surface 30. For example, as can be seen from FIG. 2A, notional surface 30 is located and sized such that the entire Z-direction height of the cross-section of plume 20 where it intersects notional surface 30 is encompassed by notional surface 30. Likewise, as can be seen from FIG. 2B, notional surface 30 is located and sized such that the entire Y-direction width of plume 20 where it intersects notional surface 30 is encompassed by notional surface 30.

Notional surface 30 may comprise an upper portion 30A and a lower portion 30B. Upper portion 30A may comprise the portion of notional surface 30 above the intersection of sampling surface 112 (as discussed further herein) and notional surface 30. Lower portion 30B may be defined as the portion of notional surface 30 below the intersection of sampling surface 112 (as discussed further herein) and notional surface 30. Where travel above an operation ceiling is restricted, it may not be possible to directly measure airborne matter 15 above the operation ceiling such that sampling surface 112 would be located at or below the operation ceiling. Likewise, where travel below an operation floor is restricted, it may not be possible to directly measure airborne matter 15 below the operation floor such that sampling surface 112 would be located at or above the operation floor.

Notional surface 30 may be located downwind of downwind edge 10B of emission source 10. In some embodiments, notional surface 30 is spaced apart from downwind edge 10B in the X-direction by a distance, d. Distance, d, may be chosen based on a number of factors. For example, distance, d, may be increased to ensure that notional surface 30 encompasses an entire cross-sectional area of plume 20 where notional surface 30 and plume 20 intersect. Distance, d, may be increased thereby increasing a minimum height of plume 20 where it intersects notional surface 30 to thereby reduce the effect of the geography (e.g., trees, manmade structures, hills and the like) on plume 20 where plume 20 intersects notional surface 30. Where emission source 10 is raised with respect to its surrounding terrain, distance, d, may be approximately 6 to 10 times the Z-direction height of emission source 10 above the surrounding terrain to mitigate airflow disturbance caused by the protrusion of emission source 10. At the same time, distance, d, may be minimized to increase the accuracy of method 100. In some embodiments distance, d, is between approximately 0 m and 500 m. In some embodiments distance, d, is greater than 500 m.

Where travel above an operation ceiling is restricted, distance, d, may be chosen such that downwind edge 20B of plume 20 intersects notional surface 30 at the same altitude as where sampling surface 112 intersects notional surface 30. Where travel above an operation ceiling is restricted, distance, d, may be chosen such that downwind edge 20B of plume 20 intersects lower portion 30B of notional surface 30, as shown in FIG. 2A. Where travel above an operation ceiling is restricted, distance, d, may be chosen such that downwind edge 20B of plume 20 intersects upper portion 30A of notional surface 30, as shown in FIG. 3. In the FIG. 3 embodiment, method 100 may have increased accuracy where distance, d, is chosen to minimize the distance between sampling surface 112 and the intersection of downwind edge 20B of plume 20 with upper portion 30A of notional surface 30.

At block 120 of FIG. 1, mass ratio measurements 122A are collected along a sampling surface 112. Mass ratio measurements 122A may comprise point concentration measurements (e.g., expressed in mass per unit volume or volume per unit volume) or integrated concentration measurements (e.g., expressed as mass per unit length squared or volume per unit length squared). As discussed further herein, mass ratio measurements 122A may be collected (e.g., in a time-synchronous manner) with position data 122B corresponding to each mass ratio measurement 122A. Together, mass ratio measurements 122A and position data 122B may comprise data 122.

In some embodiments, block 120 is performed during day light hours (e.g., after sunrise but before sunset). In some embodiments, block 120 is performed when cloud cover over sampling surface 112 is at an okta value of between approximately zero and six.

Sampling surface 112 may be bounded in plan view by boundary 114 (e.g., as shown in FIG. 2B). Boundary 114 may comprise an upwind boundary 114A, a downwind boundary 114B and lateral boundaries 114C, 114D. For simplicity, sampling surface 112 is depicted and described herein as being rectangular in plan view, but this is not mandatory and sampling surface 112 may have any regular or irregular shape. Likewise, while boundaries 114A, 114B, 114C and 114D are depicted as being straight, this is not mandatory and one or more such boundaries may be curved, segmented, irregular, etc.

In some embodiments, sampling surface 112 is generally or substantially planar (e.g., it may be desired that all concentration or integrated concentration measurements are taken at the same elevation or altitude) but this is not mandatory. In some embodiments, sampling surface 112 is non-planar such that some measurements along sampling surface 112 are to be taken at different elevations or altitudes.

Sampling surface 112 may be generally or substantially non-parallel to notional surface 30 such that despite possible variations in the shape and/or orientation of sampling surface 112, sampling surface 112 extends generally or substantially non-parallel to a general extension of notional surface 30. In some embodiments, sampling surface 112 is at an angle of between approximately 10° and 90° with respect to notional surface 30. In some embodiments, sampling surface 112 extends at an angle of between approximately 45° and 90° with respect to notional surface 30. Sampling surface 112 may be generally or substantially orthogonal to notional surface 30 such that despite possible variations in the shape and/or orientation of sampling surface 112, sampling surface 112 extends generally or substantially orthogonally to a general extension of notional surface 30. Sampling surface 112 may be generally or substantially horizontal such that despite possible variations in the shape and/or orientation of sampling surface 112, sampling surface 112 extends generally or substantially in the X and Y-directions. Sampling surface 112 may extend generally or substantially parallel to wind direction 5. In some embodiments, sampling surface 112 extends generally or substantially at an angle of between 0° and 60° or more about a Y-direction axis with respect to the horizontal and/or at an angle of between 0° and 60° or more about a X-direction axis with respect to the horizontal. In some embodiments, sampling surface 112 extends generally or substantially at an angle of between 0° and 40° or more about a Y-direction axis with respect to the horizontal and/or at an angle of between 0° and 40° or more about a X-direction axis with respect to the horizontal.

Figure 6:
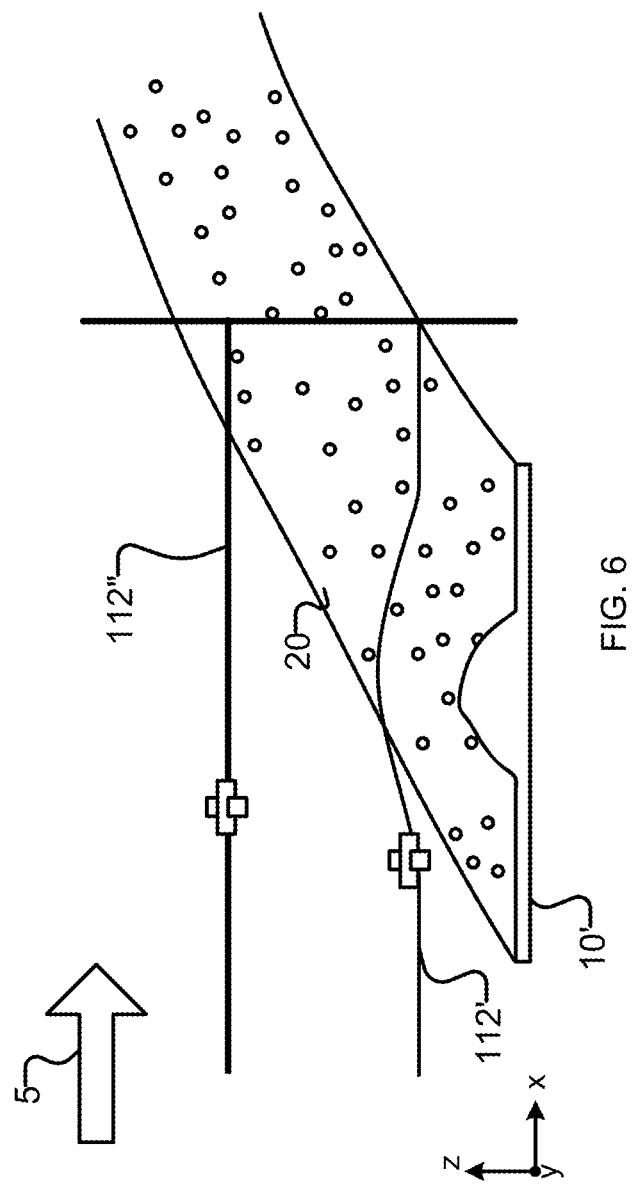
FIG. 6 is a schematic depiction of another exemplary sampling surface and another exemplary notional surface relative to another exemplary plume of airborne matter according to an embodiment of the invention.

In some embodiments, the shape and/or orientation of sampling surface 112 corresponds, at least in part, to the shape of the ground surface below sampling surface 112. For example, where there is a slope or a protrusion (e.g., hill, structure, mountain, etc.) below sampling surface 112, a shape of sampling surface 112 may imitate the slope or protrusion. In some embodiments, while the shape of sampling surface 112 may imitate the shape of the ground surface below sampling surface 112, the deviations from planarity of sampling surface 112 may be less pronounced as compared to those deviations from planarity of the ground surface. For example, where sampling surface 112 is relatively higher above the ground (e.g., above 90 m or above 120 m in altitude), the deviations from planarity of sampling surface 112 may be relatively less pronounced as compared to those of the ground surface and where sampling surface 112 is relatively lower above the ground (e.g., less than 120 m or less than 90 m in altitude), the deviations from planarity of sampling surface 112 may more closely imitate those of the ground surface. This effect may be similar to how the shape of wind flow is greatly affected by the shape of the ground surface at lower altitudes and increasingly less affected by the shape of the ground surface at higher altitudes such that at high enough altitudes, the shape of the ground does not affect the shape of the wind flow. This effect is illustrated, for example, in FIG. 6 which depicts an emission source 10' with a protrusion and two potential sampling surfaces 112', 112" at different altitudes. As can be seen from FIG. 6, sampling surface 112' mimics the protrusion of emission source 10 (although in a less pronounced way) while sampling surface 112", which is at a higher altitude than sampling surface 112', does not mimic the protrusion of emission source 10.

The shape, size and/or location of boundary 114 of sampling surface 112 may be dependent on the shape, size and/or location of emission source 10, plume 20, notional surface 30, wind speed and/or wind flow direction 5.

In some embodiments, upwind boundary 114A is farther upwind than upwind edge 10A of emission source 10. In some embodiments, upwind boundary 114A is farther upwind than the intersection of upwind edge 20A of plume 20 and sampling surface 112. In some embodiments, upwind boundary 114A has substantially the same Y-direction location as upwind edge 10A of emission source 10. In some embodiments, upwind boundary 114A is downwind of upwind edge 10A of emission source 10. In some embodiments, downwind boundary 114B is farther downwind than downwind edge 10B of emission source 10. In some embodiments, downwind boundary 114B is farther downwind than the intersection of downwind edge 20B of plume 20 and sampling surface 112. In some embodiments, downwind boundary 114B is at least as far downwind as notional surface 30. In some embodiments, downwind boundary 114B is coincident with notional surface 30 (e.g., as shown in FIG. 2B). In some embodiments, in plan view, lateral boundaries 114C, 114D encompass lateral edges 10C, 10D of emission source 10. In some embodiments, in plan view, lateral boundaries 114C, 114D encompass lateral edges 20C, 20D of plume 20. For example, in plan view, there may be a buffer between lateral boundary 114C and lateral edge 20C and a boundary between lateral boundary 114D and lateral edge 20D wherein those boundaries are sufficient to ensure that lateral edges 20C, 20D are, in plan view, within boundary 114 as shown, for example, in FIG. 2B.

In some embodiments a maximum altitude 126 of sampling surface 112 is substantially at, or just below the operation ceiling for platform 35. For example, maximum altitude 126 of sampling surface 112 may be within 10 m of the operation ceiling, within 50 m of the operation ceiling or within 100 m of the operation ceiling. By having maximum altitude 126 as close as practically possible to the operation ceiling, the accuracy of method 100 may be increased. In some embodiments, maximum altitude 126 is greater than 120 m. Where maximum altitude 126 is greater than approximately 120 m but below the top of the atmosphere's mixed layer, this may increase the accuracy of method 100 as the wind speed above 120 m can often be considered as being generally or substantially constant relative to altitude from about 120 m to the top of the atmosphere's mixed layer. In contrast, below approximately 120 m altitude, the wind speed may be subject to greater variations as a function of altitude and thus if maximum altitude 126 were to be lowered to, for example, 80 m, the lower wind speed and its effect on the flow rate of airborne matter 15 above sampling surface 112 may need to be considered in the calculation of the first mass flow rate 142 in method 100. In some embodiments, a minimum altitude of sampling surface 112 is equal to or greater than 61 m.

In some embodiments an average altitude 128 of sampling surface 112 is substantially at, or just below the operation ceiling for platform 35. For example, average altitude 128 of sampling surface 112 may be within 10 m of the operation ceiling, within 50 m of the operation ceiling or within 100 m of the operation ceiling. By having average altitude 128 as close as practically possible to the operation ceiling, the accuracy of method 100 may be increased. In some embodiments, average altitude 128 is greater than 120 m. Where average altitude 128 is greater than 120 m but below the top of the atmosphere's mixed layer, this may increase the accuracy of method 100 as the wind speed above 120 m can often be considered as being generally or substantially constant relative to altitude from about 120 m to the top of the atmosphere's mixed layer. In contrast, below approximately 120 m altitude, the wind speed may be subject to greater variations as a function of altitude and thus if average altitude 128 were to be lowered to, for example, 80 m, the lower wind speed and its effect on the flow rate of airborne matter 15 above sampling surface 112 may need to be considered in the calculation of the first mass flow rate 142.

Mass ratio measurements 122A may be collected along sampling surface 112 at block 120 by one or more instruments 40 for measuring airborne matter 15 (referred to herein as IMAM 40) as shown, for example, in FIGS. 4A, 4B and 5. IMAM 40 may be employable to measure a point concentration of airborne matter 15. Alternatively, IMAM 40 may be employable to measure an integrated concentration of airborne matter 15 where integrated concentration comprises concentration values that are integrated along a line.

IMAM 40 may operate using a measurement principle that allows for rapid measurement with high sensitivity. IMAM 40 may comprise an instrument that can measure the concentration or integrated concentration of airborne matter 15 within a range of operation and to a sensitivity that allows measurement of the extent and intensity of plume 20 of airborne matter 15. For example and not to be limiting, if plume 20 of airborne matter 15 comprising methane comprises a peak concentration of 3.4 parts per million (ppm) in air and a background concentration of 2.0 ppm, then a suitable range of operation for IMAM 40 may include 0 ppm to 10 ppm, or 0 ppm to 100 ppm, or 0 ppm to 1,000 ppm, or 0 ppm to 10,000 ppm and a sensitivity of 0.01 ppm or less.

In some embodiments, IMAM 40 comprises an optical sensing instrument. In some embodiments, IMAM 40 comprises an optical sensing instrument which emits electromagnetic radiation (e.g., infrared, visible, or ultraviolet light) and measures the absorption or modification of one or more specific wavelengths of the radiation (e.g., by airborne matter 15) to determine the concentration of airborne matter 15. The optical sensing instruments may employ an infrared source, one or more lasers with outputs of one or more specific wavelengths, or a tunable laser that can vary the wavelength of its output. In some embodiments, the optical sensing instrument may employ sunlight as an electromagnetic energy source. The optical sensing instrument may or may not include a multi-pass cell in which a laser measurement beam length is extended by reflecting surfaces in the multi-pass cell.

Non-limiting examples of IMAMs configured to collect concentration measurements comprise a Fourier transform infrared (FTIR) spectroscopy instrument from ABB Analytical Measurements™, a MIRA mid-infrared analyzer with multipass cell from *Aeris* Technologies™, a LGR off-axis integrated cavity output spectroscopy analyzer from ABB Analytical Measurements™, a cavity ring-down spectroscopy instrument from Picarro™, a GasFinder with measurement cell from Boreal Laser™, and a differential optical absorption spectroscopy (DOAS) instrument from Avantes™.

Figure 4A:
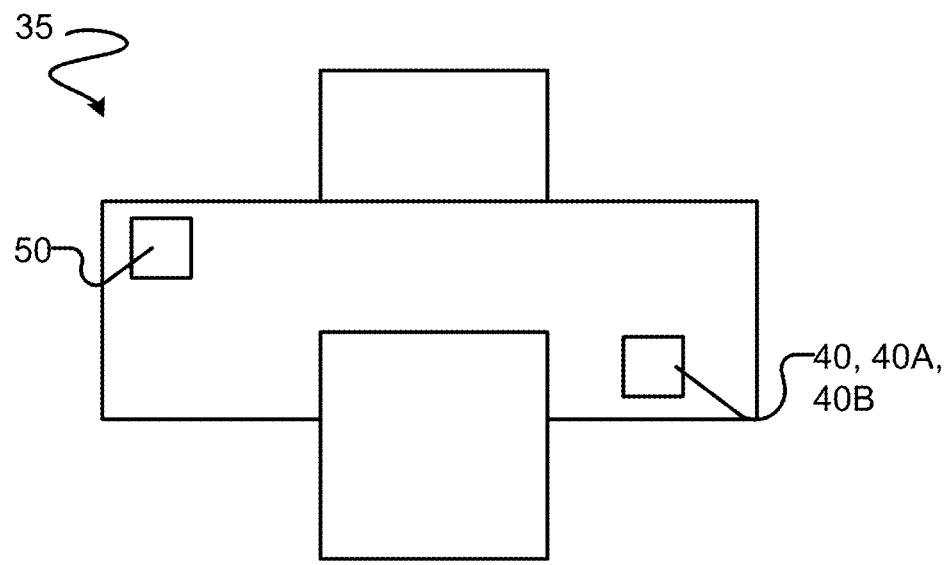
FIG. 4A is a schematic depiction of an exemplary platform according to an embodiment of the invention.

In some embodiments, IMAM 40 comprises a transmitter 40A and a receiver 40B, as shown, for example, in FIG. 4A. For example, IMAM 40 may comprise an optical sensing instrument that measures integrated concentrations with an electromagnetic beam that is transmitted from transmitter 40A across airspace toward receiver 40B. One or more than one wavelength is absorbed by airborne matter 15 between transmitter 40A and receiver 40B.

Figure 5:
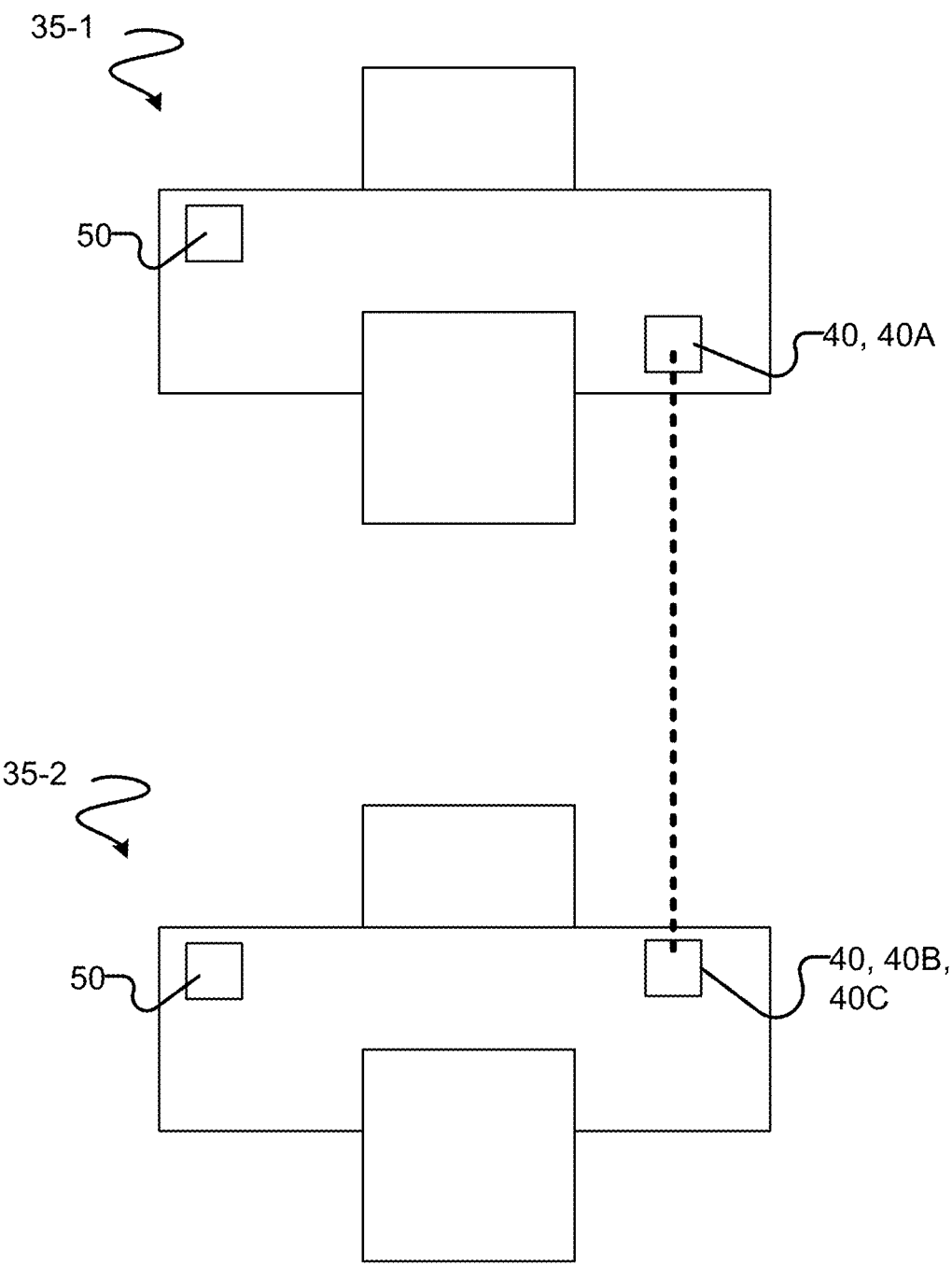
FIG. 5 is a schematic depiction of another exemplary platform according to an embodiment of the invention.

In some embodiments, IMAM 40 comprises a reflector 40C that reflects the beam from transmitter 40A back to receiver 40B. Reflector 40C may comprise the ground, a mirror, a retroreflector, vegetation, a structure, a water body, dust particles in the air or any other material that can reflect electromagnetic energy back to the receiver. In some embodiments, both transmitter 40A and receiver 40B may be mounted to primary platform 35-1. In some embodiments, reflector 40C is mounted to secondary platform 35-2, as shown, for example, in FIG. 5.

Non-limiting examples of IMAMs 40 configured for collecting integrated concentration measurements comprise open path products manufactured by Boreal Laser™ based on tunable diode laser absorption spectroscopy, Fourier Transform Infrared (FTIR) spectroscopy open path monitors, Bridger Photonics' Gas Mapping light detection and ranging (LiDAR), Pergam's LaserMethane, and differential absorption LiDAR (DIAL).

In some embodiments, IMAM 40 is supported by one or more stationary structures (e.g., a tower, building, column, or mast, etc.) nearby to emission source 10. Each structure may have one or more transmitters and/or receivers of IMAM 40. In some embodiments, a plurality of structures with receivers and/or reflectors are provided for each transmitter of IMAM 40. This is not mandatory. In some embodiments, IMAM 40 is supported by a moveable platform 35 (referred to herein simply as platform 35).

Platform 35 may comprise any suitable platform. Platform 35 may comprise an aerial platform. For example, platform 35 may comprise an UAV such as a drone or a manned aerial vehicle such as an airplane, an ultralight aircraft, a glider, a helicopter, a balloon or the like. Platform 35 may comprise a ground or water-based vehicle such as a boat, a car, a truck, a motorcycle, an all-terrain vehicle, etc. Platform 35 could comprise a person.

Where platform 35 is an unmanned vehicle such as a UAV, platform 35 may be remotely controlled (e.g., by a user, either in real time, by pre-programming or both), autonomous (pre-programmed or internally controlled), or controlled by a tether.

In some embodiments, platform 35 comprises a single vehicle. In other embodiments platform 35 may comprise a primary platform 35-1 and a secondary platform 35-2 as shown, for example, in FIG. 5. For example, primary platform 35-1 may comprise a first UAV with a transmitter of IMAM 40 while secondary platform 35-2 may comprise a second UAV with a receiver of IMAM 40 which works in conjunction with the transmitter of primary platform 35-1. As another example, primary platform 35-1 may comprise a first UAV with a transmitter and receiver of IMAM 40 while secondary platform 35-2 may comprise a second UAV with a reflector for IMAM 40 which works in conjunction with the transmitter and receiver of primary platform 35-1. As another example, primary platform 35-1 may comprise a UAV with a transmitter of IMAM 40 while secondary platform 35-2 may comprise a truck with a receiver of IMAM 40 which works in conjunction with the transmitter of primary platform 35-1. As another example, primary platform 35-1 may comprise a UAV with a transmitter and receiver of IMAM 40 while secondary platform 35-2 may comprise a truck with a reflector for IMAM 40 which works in conjunction with the transmitter and receiver of primary platform 35-1.

Figure 4B:
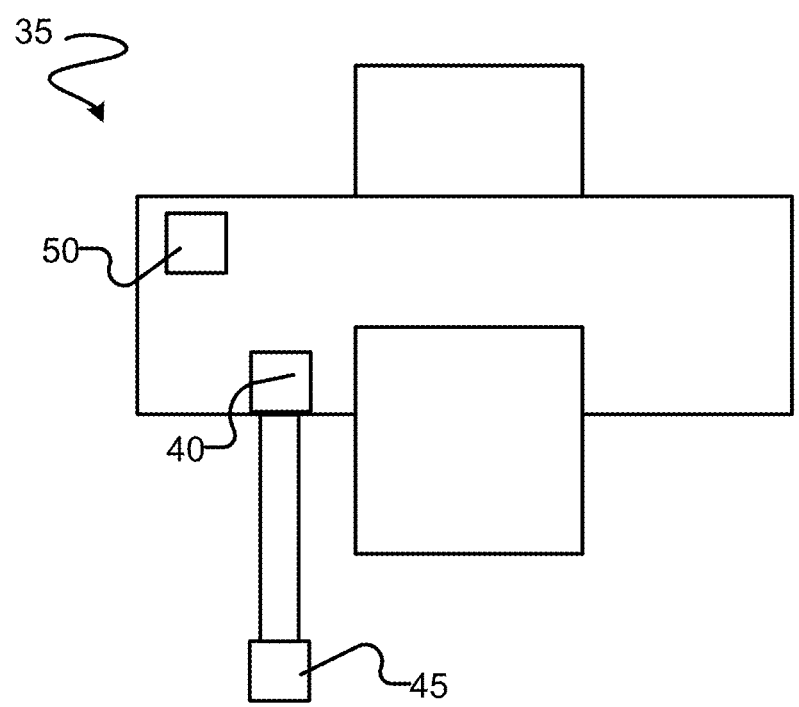
FIG. 4B is a schematic depiction of another exemplary platform according to an embodiment of the invention.

In some embodiments, at least a portion of IMAM 40 (e.g., receiver 40B of IMAM 40) is mounted directly to platform 35. However, if platform 35 comprises a rotary-blade vehicle (e.g., a helicopter, a multi-rotor drone, a propeller plane, etc.) rotor wash from the blades may disrupt the airflow and result in sampling of air by IMAM 40 that is not representative of the location. As such, in some embodiments, platform 35 may comprise one or more sample intakes 45 spaced apart from rotor wash as shown, for example in FIG. 4B so that the air sampled by IMAM 40 is representative of the air at the identified location.

In some embodiments, platform 35 may comprise a plurality of sample intakes 45. For example for concentration measurements, one sample intake 45 may be fixed to the outer edge of the left wing and another sample intake 45 may be fixed to the outer edge of the right wing of the same airplane, in an embodiment featuring wings. Such an arrangement would effectively provide for the equivalent of two platform paths with a single pass of the aircraft. In some embodiments, sample intake 45 may be attached to a dragline and towed behind and below platform 35, out of the way of the rotor wash.

To facilitate accurate data collection where platform 35 is a rotary-blade vehicle, platform 35 may also (or alternatively) be flown at a speed to minimize the effect of the rotor wash. The appropriate speed, or range of speeds that are suitable will depend on the environmental conditions (e.g., local wind speed), and the characteristics of platform 35 (size, rotor type and/or speed, and the like). For example, for a manned helicopter, platform 35 may be flown between approximately 40 km/h and 100 km/h airspeed or greater. In some embodiments, the speed may be less (e.g., less than approximately 40 km/h.

Platform 35 (e.g., primary platform 35-1 and/or secondary platform 35-2) may comprise a position sensor 50. Position sensor 50 may provide or obtain geographic position information of platform 35. For example, position sensor 50 may provide or obtain latitude and longitude or other coordinates, of platform 35. Altitude (height above ground level) or elevation (height above sea level or other specified datum) may also be part of the geographic position information collected by position sensor 50. Position sensor 50 may comprise (or employ) global navigation satellite system (GNSS), global positioning system (GPS), radar, range finder lasers, sonar, a fixed measure (e.g., a tape measure), an altimeter, etc.

Where platform 35 comprises a single vehicle, platform 35 may travel along a platform path 124 to collect mass ratio measurements 122A at block 120. Platform path 124 may travel along sampling surface 112. Platform path 124 may be dependent at least in part on the shape, size and location of sampling surface 112, wind speed and wind flow direction 5. For example, platform path 124 may be limited by boundaries 114 of sampling surface 112 and/or by the altitude along sampling surface 112. As platform path 124 covers more of sampling surface 112, the accuracy of method 100 may increase.

In some embodiments, platform path 124 starts at downwind boundary 114B and finishes at upwind boundary 114A. This may reduce the risk that a disturbed portion of plume 20 is sampled at block 120.

Figure 7:
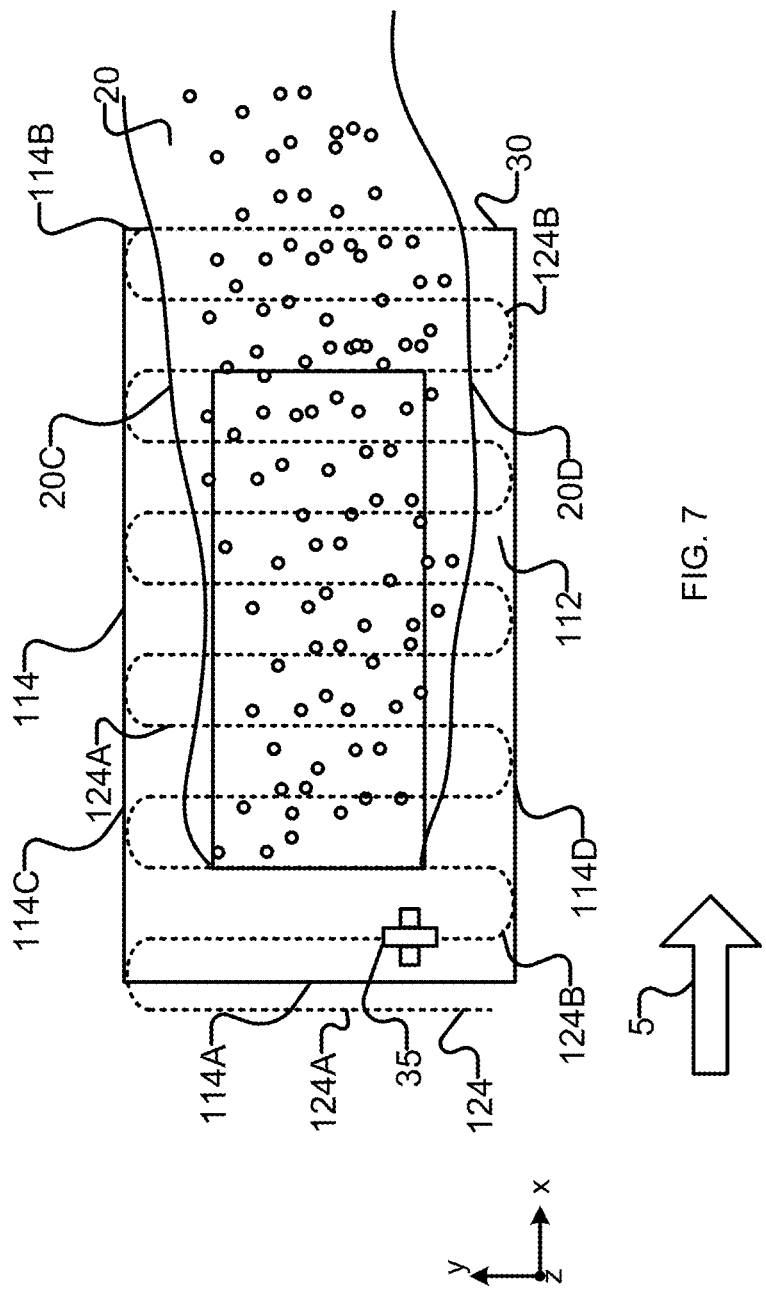
FIG. 7 is a schematic depiction of an exemplary platform path relative to an exemplary emission source according to an embodiment of the invention.

In some embodiments, platform path 124 may travel back and forth between lateral boundaries 114C, 114D as platform path 124 extends from downwind boundary 114B to upwind boundary 114A. For example, platform path 124 may comprise a plurality of generally or substantially parallel segments 124A, as shown in FIG. 7. In some embodiments, segments 124A are non-parallel. Segments 124A may be generally or substantially straight. This is not mandatory. Each segment 124A may be curved or segmented along all or a portion of its length. Segments 124A may extend generally or substantially at an angle of between approximately 20° and 90° with respect to wind flow direction 5. Segments 124A may extend generally or substantially at an angle of between approximately 90° and 60° with respect to wind flow direction 5, but this is not mandatory. Segments 124A may extend generally or substantially orthogonally to wind flow direction 5. In some embodiments, adjacent segments 124A are connected by secondary segments 124B. Secondary segments 124B may be curved. In some embodiments, each segment 124A extends from first lateral boundary 114C to second lateral boundary 114D while secondary segments 124B are located outside of boundary 114. In some embodiments, adjacent ones of the generally or substantially parallel segments 124A are spaced apart from one another in wind flow direction 5, as shown in FIG. 7. In some embodiments, adjacent segments 124A are spaced apart from one another in wind flow direction 5 by a distance of between approximately 0.1 m and 100 m or more. Smaller spacing between adjacent segments 124A may increase the accuracy of method 100.

In some embodiments, platform path 124 does not strictly travel along sampling surface 112 but instead may travel onto and off of sampling surface 112 one or more times. Where this is the case, collected data may be filtered to remove data collected away from sampling surface 112 (or outside of a threshold distance from sampling surface 112) while leaving data collected on sampling surface 112 (or within a threshold distance from sampling surface 112).

In some embodiments, where mass ratio measurements 122A comprise generally or substantially horizontally oriented integrated concentration measurements, platform path 124 may simply follow at least a portion of the perimeter of boundary 114. For example, in some embodiments, platform path 124 travels along (or parallel to) one of lateral boundaries 114C, 114D from downwind boundary 114B to upwind boundary 114A.

In some embodiments, where mass ratio measurements 122A comprise generally or substantially vertically oriented integrated concentration measurements, platform 35 may first follow platform path 124 and then platform 35 may follow a second similar shaped platform path at a second altitude (higher or lower) to obtain a second set of measurements. The difference between the corresponding first and second measurements could then be taken to obtain integrated concentrations. An average point concentration could then be determined for the altitude range between the first and second altitudes.

Figure 8:
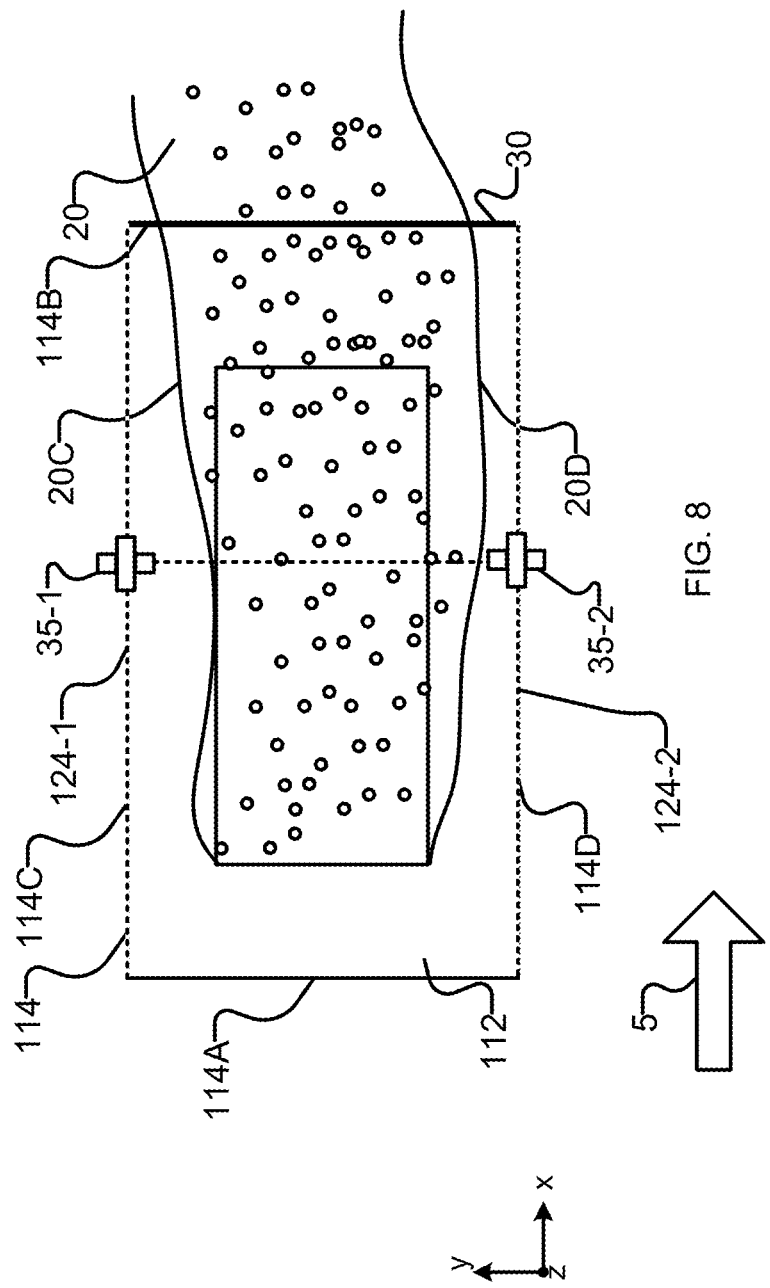
FIG. 8 is a schematic depiction of another exemplary platform path relative to an exemplary emission source according to an embodiment of the invention.

In some embodiments, the altitude that platform 35 travels along platform path 124 (or primary and secondary platform paths 124-1, 124-2 as shown, for example, in FIG. 8) follows sampling surface 112. However, it should be understood that due to practical constraints, the actual path travelled at block 120 may have some variation in altitude, notably due to inflight conditions (e.g., wind, turbulence, changes in flight control, etc.) that may cause altitude variations from sampling surface 112 when following platform path 124.

Where platform 35 comprises a primary platform 35-1 and a secondary platform 35-2, primary platform 35-1 may travel along a primary platform path 124-1 and secondary platform 35-2 may travel along a secondary platform path 124-2 to collect mass ratio measurements 122A at block 120. Primary platform path 124-1 and secondary platform path 124-2 may each travel along sampling surface 112. Primary platform path 124-1 and secondary platform path 124-2 may each be dependent at least in part on the shape, size and location of sampling surface 112, wind speed and wind flow direction 5. For example, Primary platform path 124-1 and secondary platform path 124-2 may each be limited by boundaries 114 of sampling surface 112 and/or by the altitude along sampling surface 112.

In some embodiments, primary platform path 124-1 and secondary platform path 124-2 each start at downwind boundary 114B and finish at upwind boundary 114A. This may reduce the risk that a disturbed portion of plume 20 is sampled at block 120.

In some embodiments, primary platform path 124-1 and secondary platform path 124-2 are generally or substantially similar in shape except in that they are spaced apart from each other in one or more of the X, Y and Z-directions. For example, where primary platform 35-1 comprises a downward pointing transmitter 40A of IMAM 40, primary platform 35-1 may follow platform path 124-1 generally or substantially similar in XY plane shape to platform path 124 at a first altitude while secondary platform 35-2 follows platform path 124-2 generally or substantially similar in XY plane shape to platform path 124 but at a second lower altitude. As another example, where primary platform 35-1 comprises a horizontally pointing transmitter 40A of IMAM 40, platform path 124-1 may travel along (or generally or substantially parallel to) lateral boundary 114C from downwind boundary 114B to upwind boundary 114A while platform path 124-2 of secondary platform 35-2 travels along (or generally or substantially parallel to) lateral boundary 114D from downwind boundary 114B to upwind boundary 114A, as shown in FIG. 8.

In some embodiments, IMAM 40 is configured to continuously record mass ratio measurements 122A of airborne matter 15 along platform path 124. In some embodiments, IMAM 40 is configured to record mass ratio measurements 122A of airborne matter 15 at discrete and frequent intervals along platform path 124. For example, some embodiments, IMAM 40 is configured to record mass ratio measurements 122A of airborne matter 15 at greater than 0.5 Hz (for example about 0.5 Hz, 1 Hz, 10 Hz, 100 Hz, 1,000 Hz, 10,000 Hz or any value in between or beyond). Intervals below 0.5 Hertz may also be possible. For each mass ratio measurement 122A obtained by IMAM 40, a position sensor 50 may record corresponding position data 122B.

Together, mass ratio measurements 122A and position data 122B may be processed to create a two-dimensional (or three-dimensional) mass ratio map for sampling surface 112.

In some embodiments, despite variations in altitude of platform path 124 (whether purposeful or due to practical constraints), platform path 124 and the resultant data 122 may be assumed to have a constant representative altitude. The representative altitude may be equal to the maximum altitude 126, average altitude 128, an altitude 129 where sampling surface 112 intersects notional surface 30 or another altitude representative of platform path 124. Employing a representative altitude is not mandatory and instead actual altitude measurements for each mass ratio measurement 122A could be employed. However, such an assumption may simplify one or more remaining steps of method 100. For convenience, method 100 is described herein with the assumption that platform path 124 and resulting data 122 has a constant altitude or elevation equal to altitude 29.

Block 130 comprises determining a scaling factor 132. Scaling factor 132 may be employable to determine first mass flow rate 142 of airborne matter 15 through upper portion 30A of notional surface 30 at block 140 based on data 122, as discussed further herein. Where upwind edge 20A of plume 20 intersects upper portion 30A of notional surface 30 and downwind edge 20B of plume 20 intersects lower portion 30B of notional surface 30 as shown in FIG. 2A, scaling factor 132 may be determined according to Equation 1:

$$S = \frac{\lambda}{\delta} \quad \text{(Equation 1)}$$

where λ is a distance between the intersection of upwind edge 20A of plume 20 with notional surface 30 and altitude 129 where sampling surface 112 intersects with notional surface 30, as shown in FIG. 2A and δ is a distance between notional surface 30 and the intersection of upwind edge 20A of plume 20 with sampling surface 112, as shown in FIG. 2A.

Where upwind edge 20A and downwind edge 20B of plume 20 both intersect upper portion 30A of notional surface 30 as shown in FIG. 3, scaling factor 132 may be determined according to Equation 2:

$$S = \frac{\lambda'}{\delta'} \quad \text{(Equation 2)}$$

where λ' is a distance between the intersection of upwind edge 20A of plume 20 with notional surface 30 and the intersection of downwind edge 20B of plume 20 with notional surface 30, as shown in FIG. 3 and δ' is a distance between the intersection of downwind edge 20B of plume 20 with sampling surface 112 and the intersection of upwind edge 20A of plume 20 with sampling surface 112, as shown in FIG. 3.

The location of the intersection of upwind edge 20A of plume 20 with notional surface 30 may be determined by any suitable manner. In some embodiments, the intersection of upwind edge 20A of plume 20 with notional surface 30 may be determined visually (e.g., where plume 20 is visible to the human eye, to a camera, etc.). In some embodiments, the intersection of upwind edge 20A of plume 20 with notional surface 30 may be determined by piloting a vehicle (e.g., an aerial vehicle) with an IMAM to the intersection of upwind edge 20A and notional surface 30 and recording the location. In some embodiments, the intersection of upwind edge 20A of plume 20 with notional surface 30 may be extrapolated based on a position of upwind edge 20A of plume 20 at or below sampling surface 112. In some embodiments, the intersection of upwind edge 20A of plume 20 with notional surface 30 may be extrapolated based on the slope of upwind edge 20A of plume 20 at or below sampling surface 112. In some embodiments, the intersection of upwind edge 20A of plume 20 with notional surface 30 may be extrapolated based at least in part on a location of upwind edge 10A of emission source 10.

In some embodiments, the position and/or slope of upwind edge 20A of plume 20 below sampling surface 112 is determined based on one or more mass ratio measurements taken below sampling surface 112 by, for example, IMAM 40. Such mass ratio measurements may be obtained by causing platform 35 to collect further mass ratio measurements and position data below sampling surface 112. In some embodiments, platform 35 travels along one or more paths similar in shape (but lower in altitude) as compared to platform path 124 to collect such mass ratio measurements. In some embodiments, platform 35 travels along one or more paths similar in shape (but lower in altitude) as compared to a first portion of platform path 124 (e.g., a portion closer to upwind edge 20A of plume 20) to collect such mass ratio measurements. For example, for an emission source 10 on the ground level at an altitude equal to zero, a wind flow direction 5 and an average altitude 128 of 120 m, further concentration measurements may also be obtained at 50 m and 80 m in altitude to identify the position of upwind edge 20A of plume 20. The position of upwind edge 20A can then be extrapolated to the location where upwind edge 20A of plume 20 intersects notional surface 30.

The extrapolation of upwind edge 20A to determine the location of the intersection of upwind edge 20A of plume 20 with notional surface 30 may employ any suitable technique. For example, the extrapolation of upwind edge 20A to determine where upwind edge 20A of plume 20 intersects notional surface 30 may employ Equation (3):

$$H = \alpha x^\beta \quad \text{(Equation 3)}$$

where H is the altitude of upwind edge 20A of plume 20 at distance, x, measured from the upwind edge 10A of emission source and the constant, α, and exponent, β, are obtained by correlation using, for example, distance, x, of upwind edge 20A at various altitudes at and below sampling surface 112.

In some embodiments, the intersection of upwind edge 20A of plume 20 with notional surface 30 may be determined using plume rise calculation methodologies known in the art. In some embodiments, the intersection of upwind edge 20A of plume 20 with notional surface 30 may be determined by extrapolating other distinct plume features, such as from a particularly elevated point source within an overall larger area emission source such as an industrial plant. This additional data could be obtained by platform 35 (or primary and secondary platforms 35-1, 35-2) or by other platforms travelling along platform paths spaced apart from sampling surface 112.

Alternatively, one of many dispersion or computational fluid dynamics models available in the art, such as AERMOD, CALPUFF, or Ansys Fluids could be using the data obtained to estimate where upwind edge 20A of plume 20 intersects notional surface 30. The location where upwind edge 20A of plume 20 intersects notional surface 30 could also be determined by applying one or more mass balance methods such as those disclosed in Canadian Patent No. 2,715,677 using an aerial platform that is authorized to be above the operation ceiling to at least the altitude of the upwind edge 20A of plume 20 to assist in correlating the extrapolation of data at lower altitudes.

If site conditions warrant, λ can be multiplied by an adjustment factor to account for atypical terrain or atmospheric stability conditions (e.g., low wind speed). As a non-limiting example, an adjustment factor may need to be applied for statically stable atmospheric conditions if there is an inversion layer that is near the altitude of sampling surface 112 or if a large plume reaches the top of the atmospheric mixed layer.

In some embodiments, scaling factor 132 may be calculated as the ratio of the vertical speed of plume 20 in the Z-direction (or rate of vertical movement) through sampling surface 112 to the wind speed. In some embodiments, scaling factor 132 may be thought of as the ratio of the mass per unit length value of airborne matter 15 in upper portion 30A of notional surface 30 to the mass per unit length value of airborne matter 15 in sampling surface 112. In some embodiments, scaling factor 132 is determined empirically.

Block 140 comprises determining a first mass flow rate 142 of airborne matter 15 through upper portion 30A of notional surface 30. In some embodiments, first mass flow rate 142 is determined based at least in part on wind speed 144, scaling factor 132, and data 122.

In some embodiments, first mass flow rate 142 is determined according to Equation 4:

$$F = M \times \omega \qquad \text{(Equation 4)}$$

where F is the first mass flow rate 142, M is a mass per unit length value in sampling surface 112 and ω is a wind factor having units of length per unit time.

Wind factor, ω, may be defined as the vertical movement of airborne matter 15 through sampling surface 112 where "vertical movement" has units of length per unit time and refers to the vertical component of the trajectory of airborne matter 15 for which travel is in an overall upward or generally or substantially upward direction or is perpendicular and upward from sampling surface 112. This includes turbulent flow with a net upwards direction.

In some embodiments, wind factor, ω is determined as the sum of an advection component and a diffusion component. The advection component may be determined, in part, by direct measurement. For example, the advection component may be determined using a sonic anemometer mounted on an aerial platform, by LIDAR or Doppler radar, or by using a dispersion model, computational fluid dynamics, or a meteorological model. The diffusion component may be modelled using atmospheric diffusion models known in the art.

In some embodiments, wind factor, ω is determined according to Equation 5:

$$\omega = W \times S \qquad \text{(Equation 5)}$$

where W is the wind speed 144 and S is scaling factor 132.

Wind speed 144 may comprise a wind speed representative of the wind speed between the intersection of sampling surface 112 with notional surface 30 and the intersection of upwind edge 20A with notional surface 30 as shown in FIG. 2A. Wind speed 144 may comprise a wind speed representative of the wind speed between the intersection of downwind edge 20B with notional surface 30 and the intersection of upwind edge 20A with notional surface 30 as shown in FIG. 3. Wind speed 144 may be determined by any suitable technique. Wind speed 144 may be determined by direct measurement (e.g., with an anemometer), remotely (e.g., by sonic detection and ranging (Sodar) instrumentation), by extrapolation of direct or remote measurements, by modelling (e.g., by air flow model, wind model, air dispersion model, meteorological model or the like), etc. In some embodiments, platform 35 (or another platform) comprises a wind sensor such as an anemometer and collects wind speed data for determining wind speed 144 (e.g., along platform path 124). In some embodiments, wind speed data is logged in a time-synchronous manner with data 122.

Where mass ratio measurements 122A comprises point concentration measurements, mass per unit length, M, may be determined by integrating each point concentration of mass ratio measurements 122A with respect to the X and Y directions. The integration may include time as a variable, but this is not required. For example, the mass per unit length value, M, may be determined according to Equation 6:

$$M = \int\int_R C(X, Y, t)\, dX\, dY \qquad \text{(Equation 6)}$$

where C is a point concentration (a type of mass ratio measurement 122A), X is the wind flow direction 5, Y is the horizontal direction perpendicular to the wind flow direction, t is time, and R is the region in the XY plane that is being integrated over. Any conventional mathematical technique may be used to perform such an integration. Alternatively, a computer program that may be part of the computer-readable program instructions, such as Surfer™ (available from Golden Software™) or ArcView™ (available from ESRI™), can be used for the contouring and integration computations to produce a map, and may be an output of the method and system of the present disclosure. A map or maps in the physical sense may not be produced; rather, the map or maps may comprise a collection of digitally stored data points. The contour areas may then be integrated to obtain the mass per unit length of airborne matter in the horizontal plane.

Where mass ratio measurements 122A comprises integrated concentration measurements, mass per unit length, M, may be determined by integrating each integrated concentration measurement of mass ratio measurements 122A with respect to a direction perpendicular to the direction in which the measurements are taken. For example, where measurements are taken in the Y-direction (e.g., as shown in FIG. 8), integrated concentrations of airborne matter 15 in boundary 114 (I) may be processed according to Equation 7:

$$M = \int_b^a I(X, t)\, dX \qquad \text{(Equation 7)}$$

where I is the integrated concentration measured in the Y-direction, X is the wind flow direction, and a and b are the limits of the integration.

Other methods may be employed to determine the mass per unit length of airborne matter 15 across sampling surface 112. For example, the integration of the mass ratio measurements 122A along sampling surface 112 may be achieved by obtaining an average or weighted average of the mass ratio measurements 122A and then multiplying this by the plan area from which the mass ratio values were obtained.

Where the altitude (e.g., average altitude 128) of sampling surface 112 is relatively low such that the wind speed above sampling surface 112 may vary as a function of altitude (e.g., where the altitude of sampling surface 112 is below approximately 120 m or below approximately 90 m), then it may be desirable to apply one or more corrections to accommodate the variation of wind speed between the intersection of sampling surface 112 (e.g., average altitude 128) with notional surface 30 and the intersection of upwind edge 20A of plume 20 with notional surface 30. For example, mass ratio measurements 122A may be separated into a plurality of groupings based at least in part on the X-direction distance from notional surface 30. Equations 4, 5 and 6 (or 7 as the case may be) may then be repeated for each grouping of mass ratio measurements 122A with a different wind speed 144 applied for each grouping wherein the wind speed increases with X-direction distance from notional surface 30. The wind speed applied for each grouping may increase from the measured (or approximated) wind speed at the intersection of sampling surface 112 with notional surface 30 to the measured (or approximated) wind speed at the intersection of upwind edge 20A of plume 20 with notional surface 30. First mass flow rate 142 may then be obtained by summing or integrating the mass flow rates for all groupings.

At block 150, a second mass flow rate 152 of airborne matter 15 through lower portion 30B of notional surface 30 is determined. Where downwind edge 20B of plume 20 intersects notional surface 30 above the intersection of sampling surface 112 with notional surface 30, second mass flow rate 152 may be zero and block 150 may be skipped. Where downwind edge 20B of plume 20 intersects notional surface 30 below but near to the intersection of sampling surface 112 with notional surface 30, second mass flow rate 152 may be near zero and block 150 may be skipped. Since lower portion 30B is located below the operation ceiling, second mass flow rate 152 of airborne matter through lower portion 30B of notional surface 30 may be determined using conventional techniques.

In some embodiments, second mass flow rate 152 of airborne matter 15 through lower portion 30B of notional surface 30 may be determined by taking mass ratio measurements along a generally or substantially vertical measurement surface at or near to and generally or substantially parallel to notional surface 30 and determining second mass flow rate 152 based off such mass ratio measurements. In some embodiments, second mass flow rate 152 is determined according to a mass balance method. A mass balance method may comprise, for example, a method of mapping the mass ratio of airborne matter in a generally vertical or generally or substantially vertical surface (although it could be horizontal in some variants), and then computing a fugitive emission flow rate measurement that is based on the conservation of mass applied to one or more virtual control volume(s). Second mass flow rate 152 of airborne matter 15 through lower portion 30B of notional surface 30 may be determined according to a method as described in Canadian Patent No. 2,715,677 and/or U.S. Pat. No. 8,294,899. Second mass flow rate 152 of airborne matter 15 through lower portion 30B of notional surface 30 may be determined according to a Total Plume method as described in Canadian Patent No. 2,655,279 and/or U.S. Pat. No. 8,781,755. Second mass flow rate 152 of airborne matter 15 through lower portion 30B of notional surface 30 may be determined by Differential Absorption Lidar (DIAL). Second mass flow rate 152 of airborne matter 15 through lower portion 30B of notional surface 30 may be determined according to the radial plume mapping method such as is described in U.S. Pat. No. 6,542,242. Second mass flow rate 152 of airborne matter 15 through lower portion 30B of notional surface 30 may be determined according to United States Environmental Protection Agency's Other Test Method 10 (OTM10-optical remote sensing for emission characterization from non-point sources). Second mass flow rate 152 of airborne matter 15 through lower portion 30B of notional surface 30 may be determined according to Milly's methods as described in U.S. Pat. No. 4,135,092 and/or U.S. Pat. No. 4,204,121. Second mass flow rate 152 of airborne matter 15 through lower portion 30B of notional surface 30 may be determined according to methods described by Desjardins et. al. (Atmospheric Environment, 2004). Second mass flow rate 152 of airborne matter 15 through lower portion 30B of notional surface 30 may be determined according to methods of estimation of a mass ratio map at notional surface 30 (such as by fluid flow modelling) or by estimation of a mass per unit length value. Second mass flow rate 152 of airborne matter 15 through lower portion 30B of notional surface 30 may be determined according to methods that do not include any sampling for notional surface 30 such as methods that assume a mass per unit length value for notional surface 30 based on a proportion of a horizontal plane's mass per unit length value.

At block 160, the total mass flow rate 162 of airborne matter 15 of plume 20 through notional surface 30 (e.g., both upper and lower portions 30A, 30B of notional surface 30) is determined. Total mass flow rate 162 may be determined by summing first mass flow rate 142 and second mass flow rate 152. Where block 150 is skipped, total mass flow rate 162 may be equal to first mass flow rate 142.

Optionally, a mass flow rate of airborne matter 15 in plume 20 through a second notional surface may be obtained based at least in part on total mass flow rate 162 where the second notional surface intersects upwind edge 20A and downwind edge 20B of plume 20. In some embodiments, the mass flow rate of airborne matter 15 through the second notional surface is approximately equal to the total mass flow rate 162. In some embodiments, the mass flow rate of airborne matter 15 through the second notional surface is equal to or approximately equal to the mass flow rate through the first notional surface 142. In some embodiments, the second notional surface is generally or substantially parallel with sampling surface 112. In some embodiments, the second notional surface is generally or substantially coincident with sampling surface 112. In some embodiments, the second notional surface is non-parallel with sampling surface 112 and notional surface 30.

Figure 9:
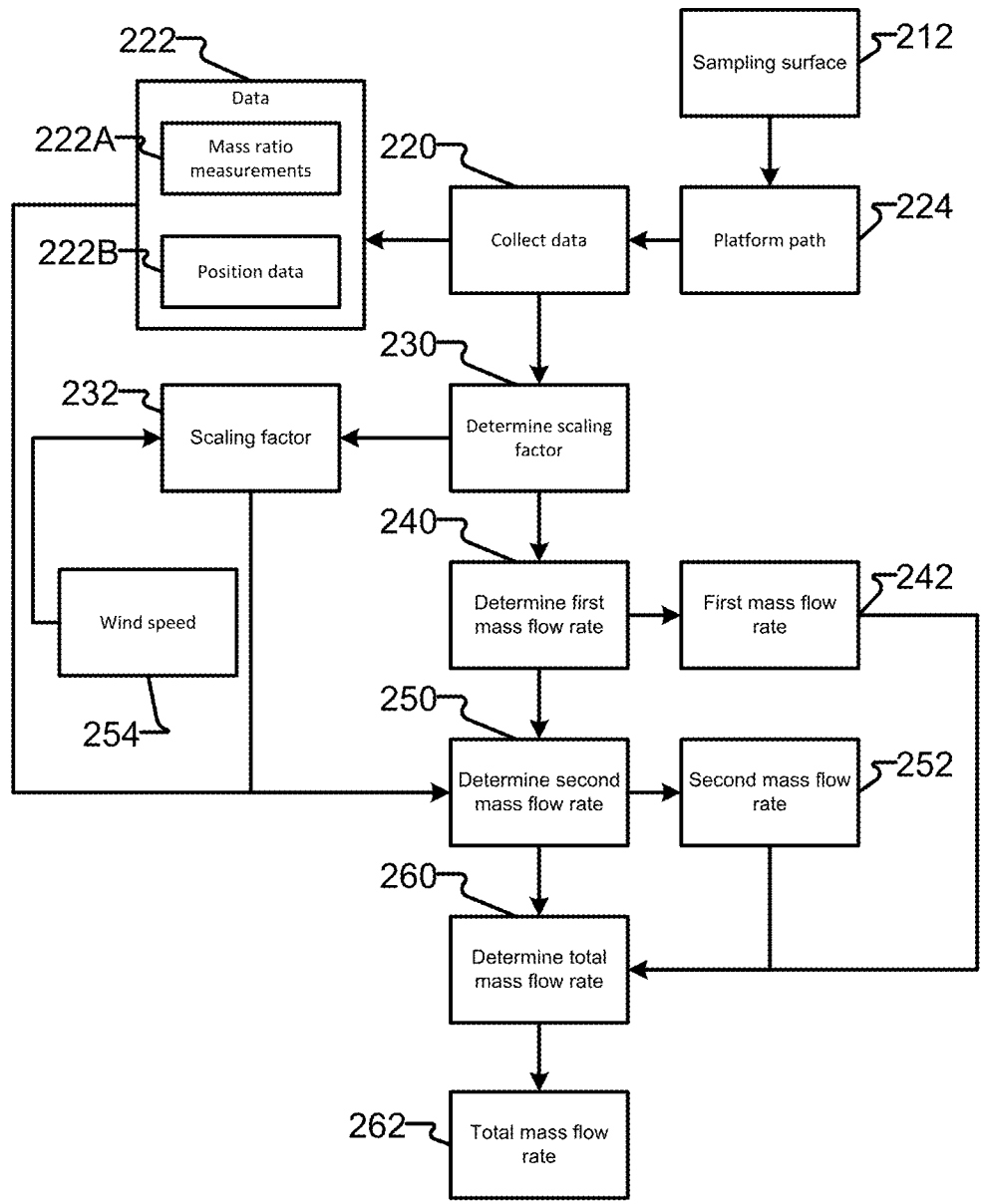
FIG. 9 depicts another exemplary method of determining a mass flow rate of airborne matter of a plume through a notional surface according to an embodiment of the invention.

FIG. 9 depicts a method 200, according to an example embodiment of the invention, for measuring the fugitive emission rate of airborne matter 15 of a plume 20 through a notional surface 30 where plume 20 is emitted from an emission source 10.

Figure 11:
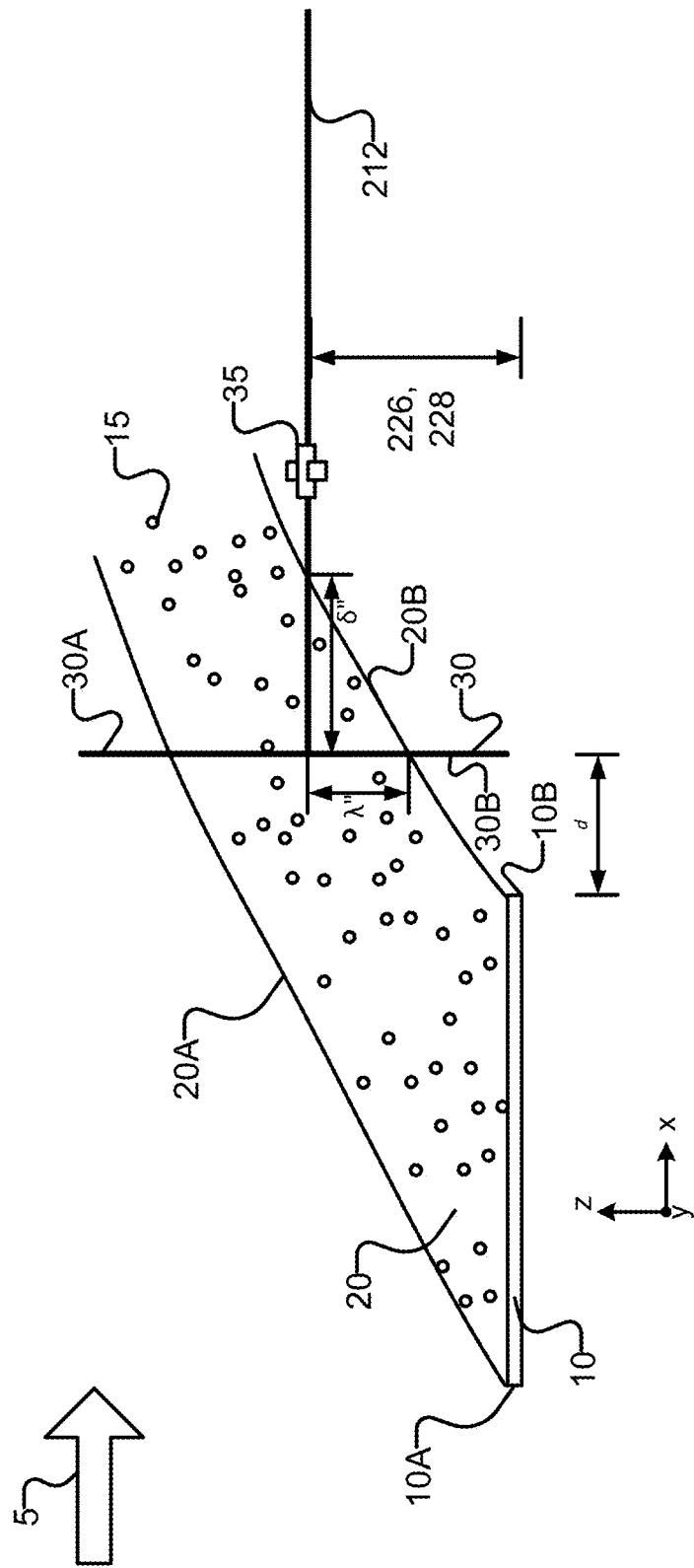
FIG. 11 is another schematic depiction of the sampling surface and the notional surface relative to the emission source of FIG. 10.

Method 200 may be employed when there is an altitude restriction for flying platform 35 below a particular altitude (referred to herein as an "operation floor"). Such restrictions may be practical (e.g., due to inherent limitations of platform 35, weather, etc.), self-imposed (e.g., for safety or cost reasons) and/or legal (e.g., due to regulations governing operation of platform 35).

Where travel below an operation floor is restricted, distance, d, between emission source 10 and notional surface 30 may be chosen such that upwind edge 20A of plume 20 intersects notional surface 30 at same altitude as where sampling surface 112 intersects notional surface 30. Where travel below an operation floor is restricted, distance, d, may be chosen such that upwind edge 20A of plume 20 intersects upper portion 30A of notional surface 30, as shown in FIG. 11.

Method 200 may be substantially similar to method 100. Specifically, unless otherwise specified, blocks 220 to 260 of method 200 are substantially similar to blocks 120 to 160 of method 100.

Figure 13:
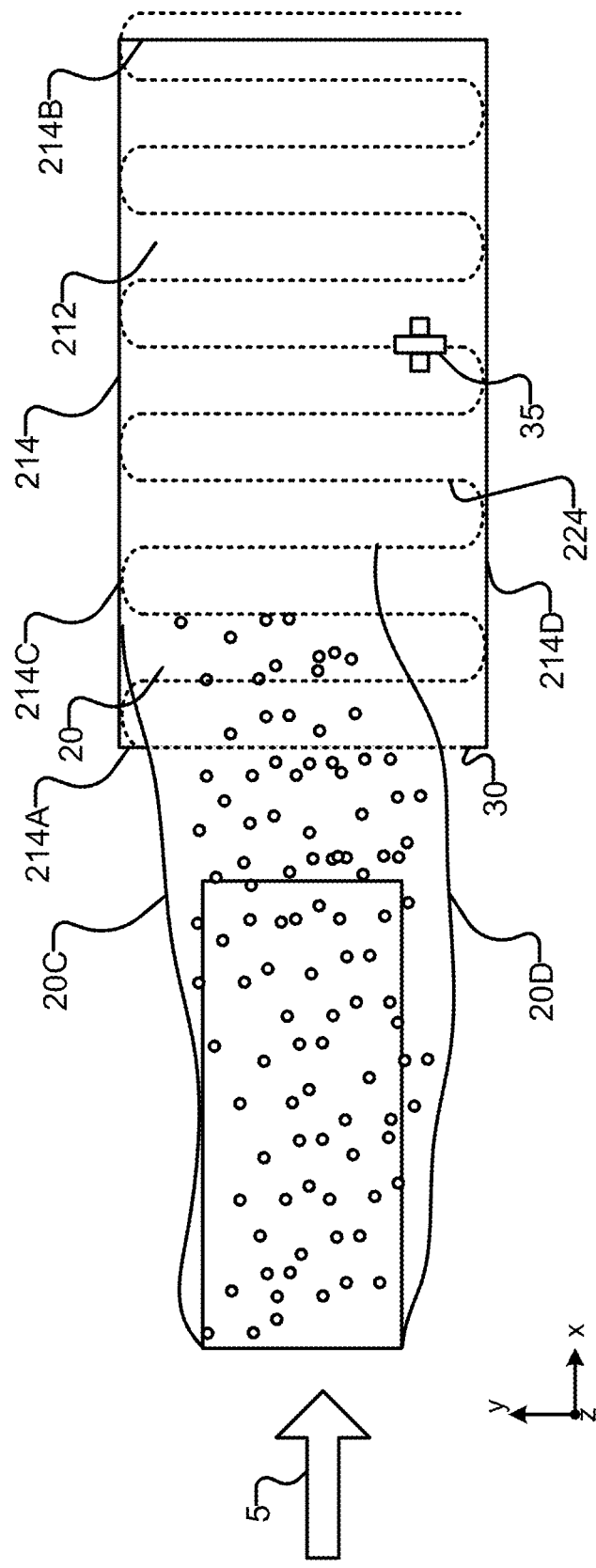
FIG. 13 is a schematic depiction of another exemplary platform path relative to an exemplary emission source according to an embodiment of the invention.
Figure 14:
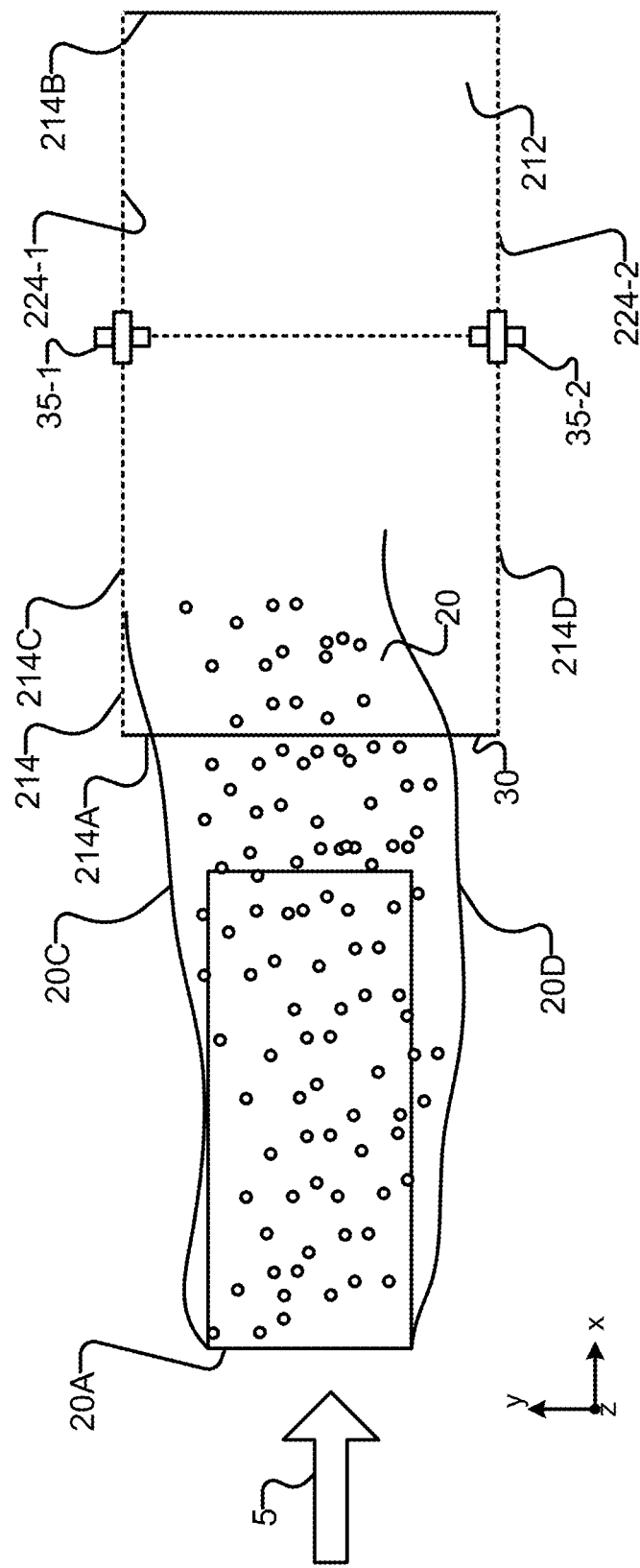
FIG. 14 is a schematic depiction of another exemplary platform path relative to an exemplary emission source according to an embodiment of the invention.

At block 220, data 222 (comprising mass ratio measurements 222A and corresponding position data 222B) is collected along sampling surface 212. Data 222 may be collected at block 220 by IMAM 40 as platform 35 travels along a platform path 224 within sampling surface 212, as shown in FIG. 13 or as primary and secondary platforms 35-1, 35-2 travel along primary and secondary platform paths 224-1, 224-2 as shown in FIG. 14.

Sampling surface 212 may be bounded in the X and Y-directions by boundary 214. Boundary 214 may comprise an upwind boundary 214A, a downwind boundary 214B and lateral boundaries 214C, 214D as shown, for example, in FIG. 10. Sampling surface 212 may be substantially similar to sampling surface 112 except as follows.

Figure 10:
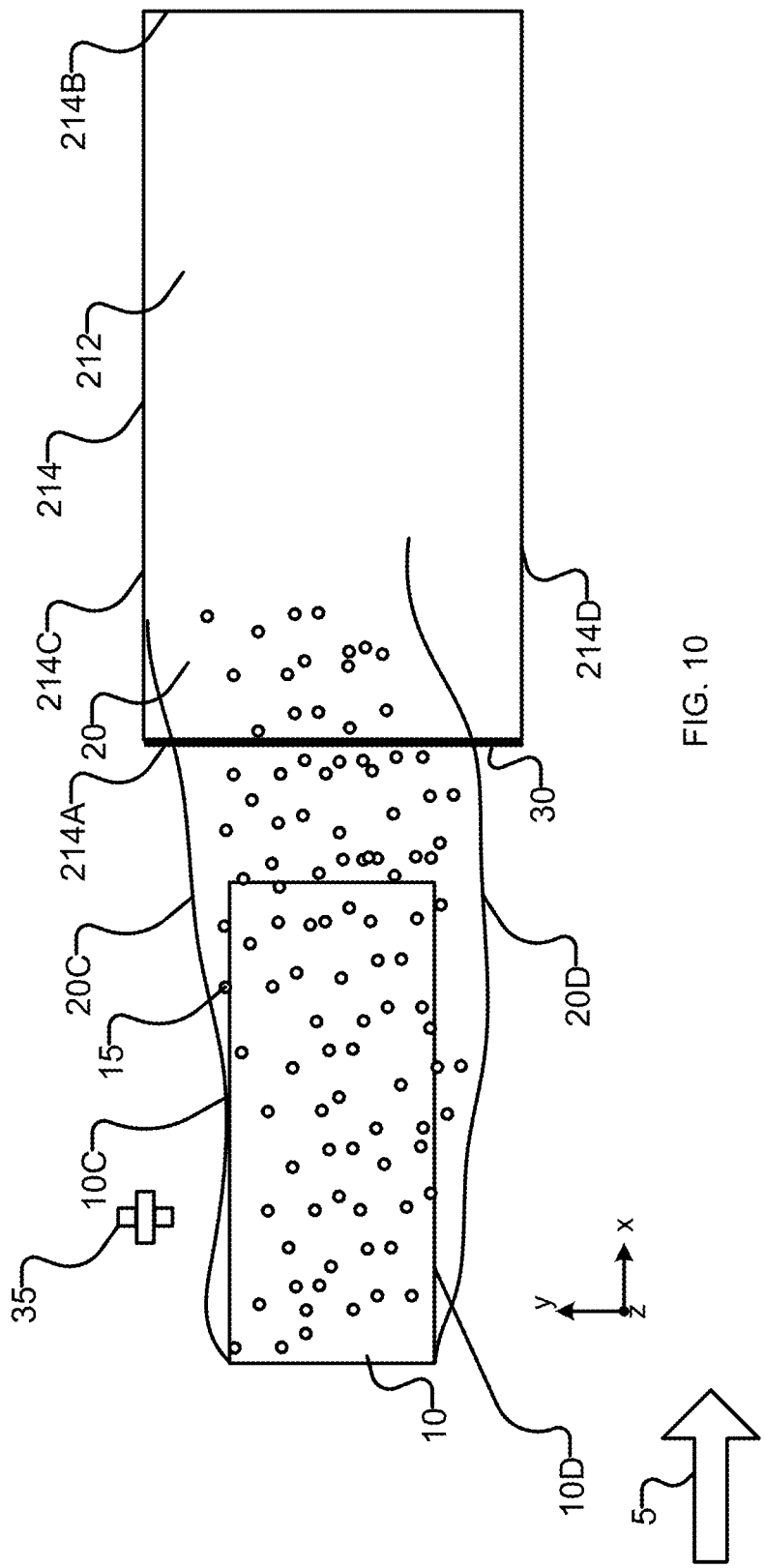
FIG. 10 is a schematic depiction of another exemplary sampling surface and another exemplary notional surface relative to an emission source according to an embodiment of the invention.

In some embodiments, unlike sampling surface 112, sampling surface 212 may be located downwind of notional surface 30. In some embodiments, upwind boundary 214A is at least as far downwind as notional surface 30. In some embodiments, upwind boundary 214A is coincident with notional surface 30 (e.g., as shown in FIG. 10). In some embodiments, downwind boundary 214B is farther downwind than a most downwind extent of the intersection of plume 20 and sampling surface 112. In some embodiments, downwind boundary 214B is farther downwind than a most downwind extent of plume 20.

In some embodiments, minimum altitude 226 of platform path 224 may be substantially at, or just above the operation floor for platform 35. For example, minimum altitude 226 of platform path 224 may be within 10 m of the operation floor, within 50 m of the operation floor or within 100 m of the operation floor. By having minimum altitude 226 as close as practically possible to the operation floor, the accuracy of method 200 may be increased.

In some embodiments, average altitude 228 of platform path 224 may be substantially at, or just above the operation floor for platform 35. For example, average altitude 228 of platform path 224 may be within 10 m of the operation floor, within 50 m of the operation floor or within 100 m of the operation floor. By having average altitude 228 as close as practically possible to the operation floor, the accuracy of method 100 may be increased.

Where platform 35 is employed at block 220, platform path 224 may be substantially similar to platform path 124 except in that platform path 224 is located along sampling surface 212 rather than sampling surface 112. For example, FIG. 13 depicts a platform path 224 substantially similar to platform path 124 of FIG. 7.

Where primary and secondary platforms 35-1, 35-2 are employed at block 220, primary and secondary platform paths 224-1, 224-2 of primary and secondary platforms 35-1, 35-2 may be substantially similar to primary and secondary platform paths 124-1, 124-2 except in that one or both of primary and secondary platform paths 224-1, 224-2 are located along sampling surface 212 rather than sampling surface 112. FIG. 14 depicts exemplary primary and secondary platform paths 224-1, 224-2 substantially similar to platform paths 124-1, 124-2 of FIG. 8.

Figure 12:
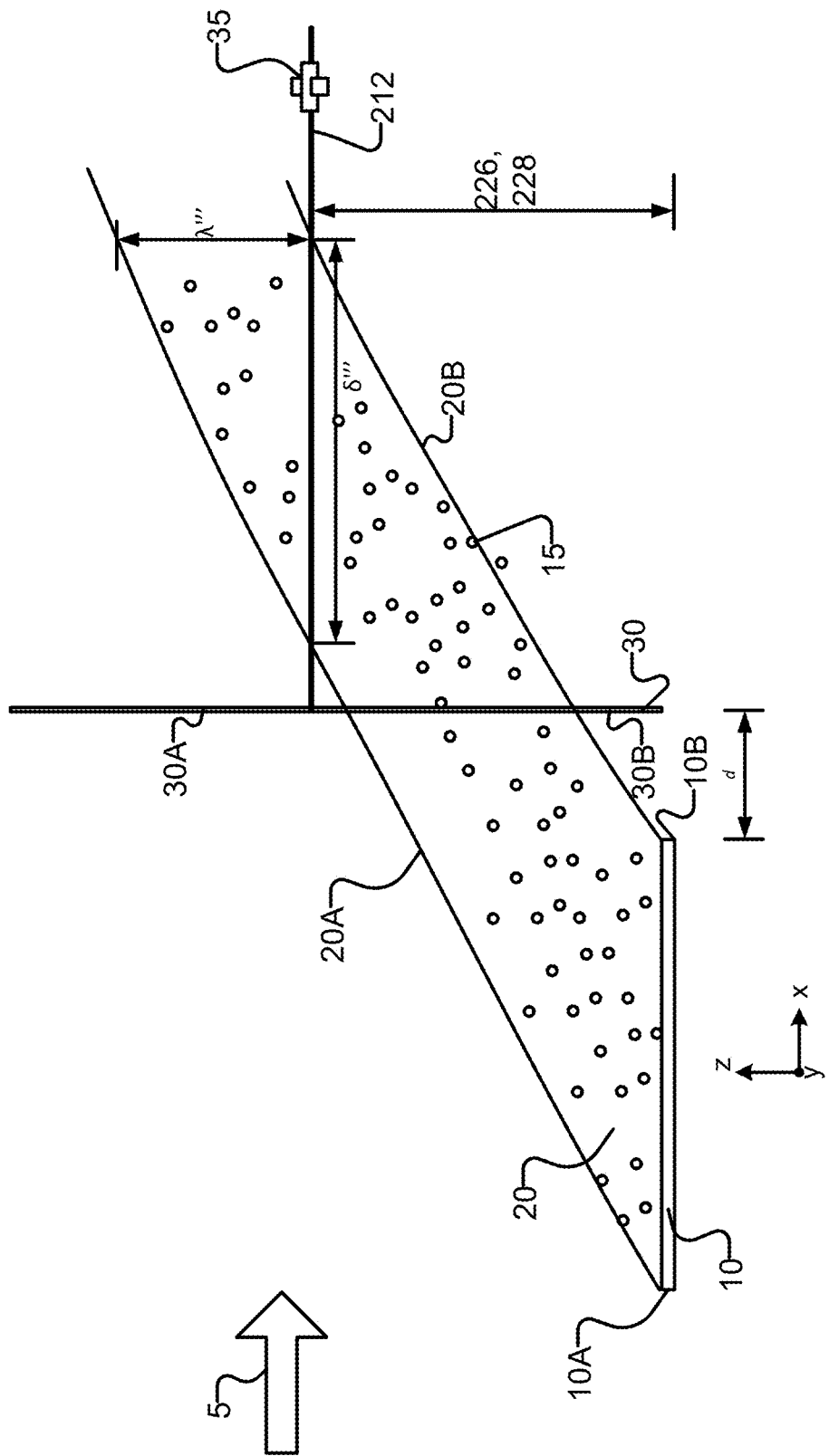
FIG. 12 is a schematic depiction of another exemplary sampling surface and another exemplary notional surface relative to another exemplary plume of airborne matter according to an embodiment of the invention.

At block 230, a scaling factor 232 is determined. Scaling factor 232 may be dependent on whether or not upwind edge 20A of plume 20 intersects sampling surface 212. In some instances, downwind edge 20B of plume 20 intersects sampling surface 212 while upwind edge 20A of plume 20 does not, such as is shown in FIG. 11. In some instances, both upwind edge 20A and downwind edge 20B of plume 20 intersect sampling surface 212 as shown in FIG. 12.

Where downwind edge 20B of plume 20 intersects sampling surface 212 while upwind edge 20A of plume 20 does not, scaling factor 232 may be determined according to Equation 8:

$$S = \frac{\lambda''}{\delta''} \quad \text{(Equation 8)}$$

where $\lambda''$ is a distance between the intersection of sampling surface 212 with notional surface 30 and the intersection of downwind edge 20B with notional surface 30, as shown in FIG. 11 and $\delta'$ is a distance between notional surface 30 and the intersection of downwind edge 20B of plume 20 with sampling surface 212 as shown in FIG. 11.

The location of the intersection of downwind edge 20B with notional surface 30 may be determined by any suitable manner. In some embodiments, the location of the intersection of downwind edge 20B with notional surface 30 is determined by analogous methods to those disclosed herein for determining the location of upwind edge 20A with notional surface 30. In some embodiments, the location of the intersection of downwind edge 20B with notional surface 30 is determined visually (e.g., where plume 20 is visible to the human eye or by camera). In some embodiments, the location of the intersection of downwind edge 20B with notional surface 30 is determined by piloting a vehicle (e.g., an aerial vehicle) to the intersection of downwind edge 20B with notional surface 30 and recording the location. In some embodiments, the location of the intersection of downwind edge 20B with notional surface 30 is determined by interpolating between the location of downwind edge 10B of emission source 10 and the intersection of downwind edge 20B of plume 20 with sampling surface 212 (e.g., as determined analyzing data 222).

Where both upwind edge 20A and downwind edge 20B of plume 20 intersect sampling surface 212, scaling factor 232 may be determined according to Equation 9:

$$S = \frac{\lambda'''}{\delta'''} \quad \text{(Equation 9)}$$

where $\lambda'''$ is a distance between the intersection of downwind edge 20B with sampling surface 212 and the intersection of upwind edge 20A with a line orthogonal to sampling surface 212 extending from the intersection of downwind edge 20B with sampling surface 212 and $\delta'''$ is a distance between the intersection of upwind edge 20A with sampling surface 212 and the intersection of downwind edge 20B with sampling surface 212, as shown in FIG. 12.

Block 240 comprises determining a first mass flow rate 242 of airborne matter 15 through upper portion 30A of notional surface 30. Where plume 20 does not intersect upper portion 30A such as in the FIG. 12 scenario, first mass flow rate 242 of airborne matter 15 through upper portion 30A of notional surface 30 is zero and block 240 may be skipped. Where plume 20 intersects upper portion 30A such as in the FIG. 11 scenario, first mass flow rate 242 of airborne matter 15 through upper portion 30A of notional surface 30 may be determined in a similar manner to how second mass flow rate 152 of airborne matter 15 through lower portion 30B of notional surface 30 is determined. For example, first mass flow rate 242 may be determined by taking mass ratio measurements along a generally or substantially vertical measurement surface near to and generally or substantially parallel to notional surface 30 and determining second mass flow rate 242 based off such mass ratio measurements.

Block 250 comprises determining a second mass flow rate 252 of airborne matter 15 through lower portion 30B of notional surface 30. Second mass flow rate 252 of airborne matter 15 through lower portion 30B of notional surface 30 may be determined in a similar manner to how first mass flow rate 142 of airborne matter 15 through upper portion 30A of notional surface 30 is determined. For example, second mass flow rate 252 may be determined according to Equations 4, 5, 6 (or 7), as described herein.

Where block 250 employs Equation 6, wind speed 144 may be replaced with wind speed 254. Wind speed 254 may comprise a wind speed representative of the wind speed between where sampling surface 212 intersects notional surface 30 and where downwind edge 20B intersects notional surface 30.

Wind speed 254 may be determined by direct measurement (e.g., with an anemometer), remotely (e.g., by sonic detection or ranging (Sodar) instrumentation), by extrapolation of direct or remote measurements, by modelling (e.g., by air flow model, wind model, air dispersion model, meteorological model or the like), etc. In some embodiments, platform 35 (or another platform) comprises a wind sensor such as an anemometer and collects wind speed data for determining wind speed 254 (e.g., along platform path 224 as shown, for example, in FIG. 13). In some embodiments, wind speed data is logged in a time-synchronous manner with data 222.

Wind speed between where sampling surface 212 intersects notional surface 30 and where downwind edge 20B intersects notional surface 30 may vary as a function of altitude. As such, it may be desirable to apply one or more corrections to accommodate the variation of wind speed between where sampling surface 212 intersects notional surface 30 and where downwind edge 20B intersects notional surface 30. For example, mass ratio measurements 222A may be separated into a plurality of groupings based at least in part on the X-direction distance from notional surface 30. Equations 4, 5 and 6 (or 7 as the case may be) may then be repeated for each grouping of mass ratio measurements 222A with a different wind speed 254 applied for each grouping wherein the wind speed decreases with X-direction distance from notional surface 30. The wind speed may decrease from the measured (or approximated) wind speed at the intersection of sampling surface 212 with notional surface 30 to the measured (or approximated) wind speed at where downwind edge 20B intersects notional surface 30. Second mass flow rate 252 may then be obtained by summing or integrating the mass flow rates for all groupings.

At block 260, the total mass flow rate 262 of airborne matter 15 of plume 20 through notional surface 30 (e.g., both upper and lower portions 30A, 30B of notional surface 30) is determined. Total mass flow rate 262 may be determined by summing first mass flow rate 242 and second mass flow rate 252. Where plume 20 does not intersect upper portion 30A of notional surface 30 such as is shown in the FIG. 12 scenario, total mass flow rate 262 may be equal to second mass flow rate 252.

Optionally, a mass flow rate of airborne matter 15 in plume 20 through a second notional surface may be obtained based at least in part on total mass flow rate 262. In some embodiments, the mass flow rate of airborne matter 15 through the second notional surface is approximately equal to the total mass flow rate 262. In some embodiments, the mass flow rate of airborne matter 15 through the second notional surface is equal to or approximately equal to the mass flow rate through the first notional surface 252. In some embodiments, the second notional surface is generally or substantially parallel with sampling surface 212. In some embodiments, the second notional surface is generally or substantially coincident with sampling surface 212.

In some embodiments, it may be desirable to account for a background concentration of airborne matter 15 (e.g., from sources other than emission source 10) such that the total mass flow rate (e.g., total mass flow rate 162 or total mass flow rate 262) doesn't reflect the presence of airborne matter 15 from sources other than emission source 10. To account for a background concentration of airborne matter 15, it may be useful to measure the concentration of airborne matter 15 at one or more locations that in plan view are outside boundary 114 (or boundary 214 as the case may be). For example, it may be useful to measure the concentration of airborne matter upwind of emission source 10. This background concentration value may be subtracted from the mass ratio measurements obtained at blocks 120, 220 (e.g., mass ratio measurements 122A or 222A) within boundary 114 (or boundary 214 as the case may be) to account for such background concentrations of airborne matter 15.

Alternatively, the mass flow rate of background airborne matter 15 flowing over emission source 10 from upwind (and through notional surface 30) may be determined according to, for example, methods disclosed herein, a mass balance method, or other methods known in the art and this background mass flow rate may be subtracted from the total mass flow rate through notional surface 30 (e.g., total mass flow rate 162 or total mass flow rate 262). The mass flow rate of background airborne matter 15 flowing over emission source 10 from upwind (and through notional surface 30) may be determined by determining the mass flow rate of airborne matter 15 flowing through a measurement surface (substantially similar to notional surface 30) located upwind of (but near to) emission source 10.

In some embodiments, platform 35 (or primary and secondary platforms 35-1, 35-2) may be caused to travel along a sampling surface (similar to sampling surfaces 112, 212) having a relatively larger area while obtaining mass ratio measurements. The relatively larger area may contain a plurality of emission sources and/or plumes. In some cases, the number and/or location of the emissions sources and/or plumes in the relatively larger area may be unknown. The collected mass ratio measurements may be studied to identify plumes and/or emission sources (e.g., by identifying regions having relatively higher mass ratio measurements) and the relevant data for each identified plume or emission source may then be used according to methods described herein to determine mass flow rates for each identified plume and/or emission source.

In some embodiments, the mass ratio measurements or the mass per unit length value determined from mass ratio measurements in a sampling surface located between 0 m and 50 m above the surface of an emission source is used for a correlation to the total mass flow rate determined by method 100 or method 200.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

Interpretation of Terms

Unless the context clearly requires otherwise, throughout the description and the

- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms. These terms ("a", "an", and "the") mean one or more unless stated otherwise;
- "and/or" is used to indicate one or both stated cases may occur, for example A and/or B includes both (A and B) and (A or B);
- where a feature is described as being "optional" or "optionally" present or described as being present "in some embodiments" it is intended that the present disclosure encompasses embodiments where that feature is present and other embodiments where that feature is not necessarily present and other embodiments where that feature is excluded. Further, where any combination of features is described in this application this statement is intended to serve as antecedent basis for the use of exclusive terminology such as "solely," "only" and the like in relation to the combination of features as well as the use of "negative" limitation(s)" to exclude the presence of other features; and
- "first" and "second" are used for descriptive purposes and cannot be understood as indicating or implying relative importance or indicating the number of indicated technical features.

Words that indicate directions such as "vertical", "transverse", "horizontal", "upward", "downward", "forward", "backward", "inward", "outward", "left", "right", "front", "back", "top", "bottom", "below", "above", "under", "upwind", "downwind" and the like, used in this description and any accompanying claims (where present), depend at least in part on the specific orientation of the apparatus described and illustrated. The subject matter described herein may assume various alternative orientations or configurations. Accordingly, these directional terms are not strictly defined and should not be interpreted narrowly.

Where a range for a value is stated, the stated range includes all sub-ranges of the range. It is intended that the statement of a range supports the value being at an endpoint of the range as well as at any intervening value to the tenth of the unit of the lower limit of the range, as well as any subrange or sets of sub ranges of the range unless the context clearly dictates otherwise or any portion(s) of the stated range is specifically excluded. Where the stated range includes one or both endpoints of the range, ranges excluding either or both of those included endpoints are also included in the invention.

Certain numerical values described herein are preceded by "about" or "approximately". In this context, "about" or "approximately" provides literal support for the exact numerical value that it precedes, the exact numerical value ±10%, as well as all other numerical values that are near to or approximately equal to that numerical value. Unless otherwise indicated a particular numerical value is included in "about" or "approximately" a specifically recited numerical value where the particular numerical value provides the substantial equivalent of the specifically recited numerical value in the context in which the specifically recited numerical value is presented. For example, a statement that something has the numerical value of "about 10" is to be interpreted as: the set of statements:

- in some embodiments the numerical value is 10;
- in some embodiments the numerical value is in the range of 9.0 to 11.0;

and if from the context the person of ordinary skill in the art would understand that values within a certain range are substantially equivalent to 10 because the values with the range would be understood to provide substantially the same result as the value 10 then "about 10" also includes:

- in some embodiments the numerical value is in the range of C to D where C and D are respectively lower and upper endpoints of the range that encompasses all of those values that provide a substantial equivalent to the value 10.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

As will be apparent to those of skill in the art upon reading this disclosure, each of the individual embodiments described and illustrated herein has discrete components and features which may be readily separated from or combined with the features of any other described embodiment(s) without departing from the scope of the present invention.

Any aspects described above in reference to apparatus may also apply to methods and vice versa.

Any recited method can be carried out in the order of events recited or in any other order which is logically possible. For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, simultaneously or at different times.

Various features are described herein as being present in "some embodiments". Such features are not mandatory and may not be present in all embodiments. Embodiments of the invention may include zero, any one or any combination of two or more of such features. All possible combinations of such features are contemplated by this disclosure even where such features are shown in different drawings and/or described in different sections or paragraphs. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible). This is the case even if features A and B are illustrated in different drawings and/or mentioned in different paragraphs, sections or sentences.

In some embodiments, a non-transitory, computer readable medium is provided having one or more of an application program including computer instructions configured to cause at least one server and/or at least one processor to perform the methods (or one or more steps/blocks thereof) according to any of the disclosed methods.

Method embodiments (as well as one or more steps thereof) can be configured as computer readable program instructions (corresponding to the blocks/steps/methods) and can be downloaded to respective computing/processing devices from a computer readable storage medium or to an external computer or external storage device via a network, for example, the Internet, a local area network, a wide area network and/or a wireless network.

Aspects of the present disclosure are described sometimes with reference to a flow, a flow diagram, and/or block diagram of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions, operable, for example, on one or more components (e.g., server(s), processor(s)). These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks, in accordance with embodiments of the present disclosure.

Any flowchart and block diagrams of the present disclosure are examples of architecture, functionality, and operations, of at least some of the embodiments of systems, methods, and computer readable media supported herein. In this regard, each block in the flowchart or block diagrams may represent a module, segment, or portion of instructions, which includes one or more executable instructions for implementing the specified logical function(s). It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be understood that at least some embodiments of the present disclosure can correspond to a cloud computing environment, but are not so limited, as embodiments of the present disclosure are capable of being implemented in conjunction with any other type of computing environment now known or later developed. With respect to a cloud computing environment, such is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

The invention claimed is:

1. A method of determining a flow rate of airborne matter of a plume from an emission source through a notional surface, the method comprising:
    obtaining a plurality of mass ratio measurements along a sampling surface; and
    determining a mass flow rate of the airborne matter of the plume through at least a portion of the notional surface based at least in part on the plurality of mass ratio measurements and a wind factor;
    wherein the wind factor comprises the product of a wind speed and a scaling factor;
    wherein the scaling factor is representative of a ratio of an amount of the airborne matter in the notional surface to an amount of the airborne matter in the sampling surface;
    wherein the sampling surface and the notional surface are non-parallel.

2. A method according to claim 1 wherein the notional surface is approximately orthogonal to a wind flow direction.

3. A method according to claim 1 wherein the sampling surface is substantially parallel to the wind flow direction.

4. A method according to claim 1 wherein the notional surface is at an angle of between approximately 0° and 60° to a vertical.

5. A method according to claim 1 wherein:
    obtaining a plurality of mass ratio measurements along the sampling surface comprises causing a platform to travel on a platform path along the sampling surface;
    the platform path comprises a plurality of substantially parallel segments; and the substantially parallel segments are oriented between approximately 20° and 90° to a wind flow direction.

6. A method according to claim 5 wherein the platform comprises an aerial vehicle.

7. A method according to claim 1 wherein determining the mass flow rate of the airborne matter of the plume through the at least a portion of the notional surface based at least in part on the plurality of mass ratio measurements comprises determining a first mass flow rate through a first portion of the notional surface based at least in part on the plurality of mass ratio measurements.

8. A method according to claim 7 wherein determining the mass flow rate of the airborne matter of the plume through the notional surface based at least in part on the plurality of mass ratio measurements comprises determining a second mass flow rate through a second portion of the notional surface and summing the first mass flow rate and the second mass flow rate to obtain the mass flow rate of the airborne matter of the plume through the notional surface wherein the second mass flow rate is determined based at least in part on a mass balance method.

9. A method according to claim 1 wherein determining the mass flow rate of the airborne matter of the plume through the at least a portion of the notional surface comprises integrating the mass ratio measurements across the sampling surface to obtain a mass per unit length value of the airborne matter and determining the mass flow rate of the airborne matter of the plume through the at least a portion of the notional surface based at least in part on the mass per unit length value and the wind factor.

10. A method according to claim 1 wherein the scaling factor is determined according to:

$$S = \frac{\lambda}{\delta}$$

where $\lambda$ is a distance between an altitude of a location where an upwind edge of the plume intersects the notional surface and the altitude of the sampling surface and $\delta$ is a distance between the notional surface and a location where the upwind edge of the plume crosses the sampling surface.

11. A method according to claim 10 wherein the location of the intersection of the upwind edge of the plume with the notional surface is determined by extrapolation based at least in part on a location of an intersection of the upwind edge of the plume and the sampling surface.

12. A method according to claim 1 wherein the scaling factor is determined according to:

$$S = \frac{\lambda}{\delta}$$

where $\lambda$ is a distance between the intersection of an upwind edge of the plume with the notional surface and an intersection of a downwind edge of the plume with the notional surface and $\delta$ is a distance between an intersection of the downwind edge of the plume with the sampling surface and an intersection of the upwind edge of the plume with the sampling surface.

13. A method according to claim 12 wherein the location of the intersection of the downwind edge of the plume with the notional surface is determined by extrapolation based at least in part on a location of the downwind edge of the plume at an altitude at or below the sampling surface.

14. A method according to claim 1 wherein the scaling factor is determined empirically.

15. A method according to claim 1 wherein obtaining a plurality of mass ratio measurements along the sampling surface comprises causing a platform to travel on a platform path along the sampling surface wherein an altitude of the sampling surface is at or above 61 m and at or below an operation ceiling of the platform.

16. A method according to claim 1 wherein the scaling factor is determined according to:

$$S = \frac{\lambda}{\delta}$$

where $\lambda$ is a distance between an intersection of a downwind edge of the plume with the sampling surface and a top of the plume above the intersection of the downwind edge with the sampling surface and $\delta$ is a distance between an intersection of an upwind edge of the plume with the sampling surface and the intersection of the downwind edge of the plume with the sampling surface.

17. A method of determining a flow rate of airborne matter of a plume from an emission source through a notional surface, the method comprising:
  obtaining a plurality of mass ratio measurements along a sampling surface;
  integrating the mass ratio measurements across the sampling surface to obtain a mass per unit length value of the airborne matter; and
  determining a mass flow rate of the airborne matter of the plume through at least a portion of the notional surface based at least in part on a product of the mass per unit length value and a wind factor;
  wherein the sampling surface and the notional surface are non-parallel;
  wherein the wind factor comprises the product of a wind speed and a scaling factor; and
  wherein the wind speed is representative of a wind speed at the notional surface between an altitude of the sampling surface and an altitude of an intersection of an upwind edge of the plume with the notional surface.

18. A method of determining a flow rate of airborne matter of a plume from an emission source through a notional surface, the method comprising:
  obtaining a plurality of mass ratio measurements along a sampling surface;
  integrating the mass ratio measurements across the sampling surface to obtain a mass per unit length value of the airborne matter; and
  determining a mass flow rate of the airborne matter of the plume through at least a portion of the notional surface based at least in part on a product of the mass per unit length value and a wind factor;
  wherein the sampling surface and the notional surface are non-parallel;
  wherein the wind factor comprises the product of a wind speed and a scaling factor; and
  wherein the wind speed is representative of a wind speed at the notional surface between an altitude of the sampling surface and an altitude of an intersection of a downwind edge of the plume with the notional surface.

19. A method of obtaining a flow rate, through a notional surface, of airborne matter originating from an emission source of interest, for a portion of a plume above a sampling surface that is located above ground level, comprising:

measuring the airborne matter at two or more identified locations in a substantially horizontal sampling surface using an instrument that measures airborne matter (IMAM), obtaining two or more concentration or integrated concentration measurements, a geographic position and altitude value for each of the two or more identified locations, mapping the concentration or integrated concentration measurements relative to the geographic position and altitude values for each of the two or more identified locations in the sampling surface to obtain an airborne matter concentration or integrated concentration distribution map in the sampling surface, and integrating the airborne matter concentrations or integrated concentrations distribution map across the sampling surface to obtain a mass per unit length value of the airborne matter in the sampling surface; and obtaining an airborne matter flow rate in mass per unit time for the portion of the plume above the sampling surface based at least in part on the mass per unit length value of the airborne matter in the sampling surface multiplied by a wind factor;

wherein the wind factor comprises the product of a wind speed and a scaling factor; and wherein the wind speed is representative of a wind speed at the notional surface between an altitude of the sampling surface and an altitude of an intersection of an upwind edge of the plume with the notional surface.

20. A method of determining a flow rate of airborne matter of a plume from an emission source through a notional surface, the method comprising:

obtaining a plurality of mass ratio measurements along a sampling surface; and determining a mass flow rate of the airborne matter of the plume through at least a portion of the notional surface based at least in part on the plurality of mass ratio measurements;

wherein the sampling surface extends at an angle greater than 45° and less than or equal to 90° relative to the notional surface.

* * * * *